(12) United States Patent  
Squitieri

(10) Patent No.: US 9,901,491 B2  
(45) Date of Patent: *Feb. 27, 2018

(54) PATIENT-ORIENTING ALTERNATING PRESSURE SUPPORT APPARATUS WITH LOWER EXTREMITY WEDGE

(71) Applicant: TurnCare, Inc., Palo Alto, CA (US)

(72) Inventor: Rafael P. Squitieri, Wilton, CT (US)

(73) Assignee: TURNCARE, INC., Palo Alto, CA (US)

( * ) Notice: Subject to any disclaimer, the term of this patent is extended or adjusted under 35 U.S.C. 154(b) by 919 days.

This patent is subject to a terminal disclaimer.

(21) Appl. No.: 14/313,570

(22) Filed: Jun. 24, 2014

(65) Prior Publication Data

US 2015/0164677 A1  Jun. 18, 2015

Related U.S. Application Data

(63) Continuation of application No. 14/063,861, filed on Oct. 25, 2013, now Pat. No. 8,757,165, which is a (Continued)

(51) Int. Cl.
*A61F 13/06* (2006.01)
*A47C 27/08* (2006.01)
(Continued)

(52) U.S. Cl.
CPC .......... *A61F 13/51474* (2013.01); *A61F 5/32* (2013.01); *A61F 5/34* (2013.01);
(Continued)

(58) Field of Classification Search
CPC ...... A61G 7/05; A61G 7/001; A61G 7/05776; A61G 7/1021; A61M 25/02
(Continued)

(56) References Cited

U.S. PATENT DOCUMENTS

| 4,567,887 A | 2/1986 | Couch, Jr. |
| 4,873,731 A | 10/1989 | Williamson |

(Continued)

FOREIGN PATENT DOCUMENTS

| WO | WO-1998/008473 | 3/1998 |
| WO | WO-2004/105805 A2 | 12/2004 |

(Continued)

OTHER PUBLICATIONS

International Search Report and Written Opinion, dated Jul. 23, 2013, 10 pp., for International Application No. PCT/US2013/034845, filed Apr. 1, 2013.

(Continued)

*Primary Examiner* — Tarla Patel
(74) *Attorney, Agent, or Firm* — Perkins Coie LLP

(57) ABSTRACT

Described herein are systems and apparatuses for enhanced comfort through contact pressure reduction. In particular, the systems and apparatuses disclosed herein prevent or otherwise mitigate pressure by actively orienting a patient over an anatomy-specific pressure-mitigating contact surface on which the patient rests. A pressure-mitigating contact portion of the contact surface includes a plurality of independently pressurized chambers configured in a specific geometric pattern that is designed to mitigate contact pressure between a support surface (e.g., bed or chair) and a specific anatomic region of a patient's body when the specific anatomic region of the patient's body is oriented over an epicenter of the geometric pattern. Additionally, a plurality of elevated side support portions and a wedge interconnected on the base material are configured to actively orient the specific anatomic region of the patient's body over the epicenter of the geometric pattern.

30 Claims, 9 Drawing Sheets

Related U.S. Application Data continuation-in-part of application No. 13/660,429, filed on Oct. 25, 2012, now abandoned.

(60) Provisional application No. 61/618,936, filed on Apr. 2, 2012.

(51) Int. Cl.

| | | |
|---|---|---|
| *A61F 13/514* | (2006.01) | |
| *A61F 5/32* | (2006.01) | |
| *A61F 5/34* | (2006.01) | |
| *A61G 7/057* | (2006.01) | |
| *A61G 7/07* | (2006.01) | |
| *A61F 13/15* | (2006.01) | |
| *A61F 13/505* | (2006.01) | |
| *A61F 13/512* | (2006.01) | |
| *A61F 13/513* | (2006.01) | |
| *A61F 13/515* | (2006.01) | |
| *A61F 13/64* | (2006.01) | |
| *A61F 13/84* | (2006.01) | |

(52) U.S. Cl.
CPC ...... *A61F 13/15203* (2013.01); *A61F 13/505* (2013.01); *A61F 13/512* (2013.01); *A61F 13/513* (2013.01); *A61F 13/515* (2013.01); *A61F 13/51456* (2013.01); *A61F 13/64* (2013.01); *A61F 13/84* (2013.01); *A61G 7/05776* (2013.01); *A61G 7/07* (2013.01); *A61F 2013/15024* (2013.01); *A61F 2013/15073* (2013.01); *A61F 2013/15154* (2013.01); *A61F 2013/15276* (2013.01); *A61F 2013/15552* (2013.01); *A61F 2013/5147* (2013.01); *A61F 2013/51492* (2013.01); *A61F 2013/8494* (2013.01); *A61G 2203/34* (2013.01); *A61G 2205/60* (2013.01)

(58) Field of Classification Search
USPC .... 128/846, 889, 892; 5/652, 653, 654, 615, 5/713, 715
See application file for complete search history.

(56) References Cited

U.S. PATENT DOCUMENTS

| | | |
|---|---|---|
| 5,815,864 A | 10/1998 | Sloop |
| 6,855,158 B2 | 2/2005 | Stolpmann |
| 7,017,195 B2 | 3/2006 | Buckman et al. |
| 8,726,908 B2 | 5/2014 | Squitieri |
| 8,757,165 B2 * | 6/2014 | Squitieri ............... A61F 5/34 128/892 |
| 2001/0016960 A1 | 8/2001 | Grabell et al. |
| 2002/0133877 A1 | 9/2002 | Kuiper et al. |
| 2004/0193084 A1 | 9/2004 | Ravikumar |
| 2004/0222611 A1 | 11/2004 | Fenwick et al. |
| 2005/0022305 A1 | 2/2005 | Bieganek et al. |
| 2005/0261656 A1 | 11/2005 | Garcia et al. |
| 2006/0064800 A1 | 3/2006 | Freund |
| 2008/0172797 A1 | 7/2008 | Mossbeck |
| 2009/0194115 A1 | 8/2009 | Squitieri |
| 2012/0090095 A1 | 4/2012 | Fraser |
| 2013/0019873 A1 | 1/2013 | Choi et al. |

FOREIGN PATENT DOCUMENTS

| | | |
|---|---|---|
| WO | WO-2005/112855 A2 | 12/2005 |
| WO | WO-2006/131733 A2 | 12/2006 |

OTHER PUBLICATIONS

U.S. Appl. No. 13/660,429 by Squitieri, R.P., et al., filed Oct. 25, 2012.
U.S. Appl. No. 14/063,861 by Squitieri, R.P., et al., filed Oct. 25, 2013, now U.S. Pat. No. 8,757,165 on Jun. 24, 2014.
U.S. Appl. No. 14/063,906 by Squitieri, R.P., et al., filed Oct. 25, 2013, now U.S. Pat. No. 8,726,908 on May 20, 2014.
U.S. Appl. No. 14/281,625 by Squitieri, R.P., et al., filed May 19, 2014.
Notice of Allowance dated Mar. 17, 2014, for U.S. Appl. No. 14/063,906 by Squitieri, R.P., et al., filed Oct. 25, 2013.
Notice of Allowance dated Apr. 11, 2014, for U.S. Appl. No. 14/063,861 by Squitieri, R.P., et al., filed Oct. 25, 2013.

* cited by examiner

PATIENT-ORIENTING ALTERNATING PRESSURE SUPPORT APPARATUS WITH LOWER EXTREMITY WEDGE

CROSS-REFERENCE TO RELATED APPLICATION

This application is a continuation of U.S. patent application Ser. No. 14/063,861, filed on Oct. 25, 2013, entitled "PATIENT-ORIENTING ALTERNATING PRESSURE SUPPORT APPARATUS WITH LOWER EXTREMITY WEDGE," which is a continuation-in-part of U.S. patent application Ser. No. 13/660,429, filed on Oct. 25, 2012, entitled "PATIENT-ORIENTING ALTERNATING PRESSURE DECUBITUS PREVENTION SUPPORT APPARATUS," which claims priority to and benefit of U.S. Provisional Patent Application Ser. No. 61/618,936, which was filed on Apr. 2, 2012, entitled "PATIENT-ORIENTING ALTERNATING PRESSURE DECUBITUS PREVENTION PILLOW," the contents of which are expressly incorporated by reference herein.

TECHNICAL FIELD

At least one embodiment of the present invention pertains to medical prevention and treatment devices, and more particularly to systems, methods, and/or apparatuses for the prevention and treatment of decubitus ulcers. Alternatively or additionally, at least one embodiment of the present invention pertains more generally to enhanced comfort through contact pressure reduction.

BACKGROUND

Decubitus ulcers (commonly known as pressure ulcers) are a frequent but often avoidable complication in many bed bound or wheelchair bound individuals. These pressure skin ulcerations typically occur as a result of steady pressure in one location on the body such as, for example, the sacrum, most notably in patients who are in bed for prolonged periods of time. Often times these patients are older, malnourished and incontinent, all factors predisposing patients to skin break down and ulceration. These patients are often not ambulatory and sit for prolonged periods of time in the same position either in bed or in a wheelchair. These individuals often are unable to reposition themselves to alleviate the pressure. Consequently, the pressure on the skin eventually causes ischemia or lack of blood flow to the area and skin breakdown results. Once the ulceration has formed and the skin barrier is broken, infection may more readily enter the body and cause infection and sepsis. The resulting infection often times leads to further disability, and in some cases, death.

There are many support surfaces on the market for the prevention of pressure ulcers. However, current support surfaces have many deficiencies including the lack of the ability to control the spatial relationship between the patient and the therapeutic surface (or contact surface) and thus patients using these support surfaces may still end up with pressure ulcer complications. Accordingly, a need exists for a system that overcomes the above problems, as well as one that provides additional benefits.

Overall, the examples herein of some prior or related systems and their associated limitations are intended to be illustrative and not exclusive. Other limitations of existing or prior systems will become apparent to those of skill in the art upon reading the following.

SUMMARY

Described herein are systems and apparatuses for the prevention and treatment of pressure ulcers. In particular, the ulcer prevention systems and/or apparatuses disclosed herein prevent or otherwise mitigate pressure ulcers by at least actively orienting a patient over an anatomy-specific pressure-mitigating contact surface on which the patient rests. Alternatively or additionally, the systems and apparatuses can be utilized for improving comfort through contact pressure mitigation.

In one embodiment, a contact pressure-mitigation support apparatus includes a base material, a pressure-mitigating contact portion, a plurality of elevated side support portions, and a wedge portion. The pressure-mitigating contact portion includes a plurality of independently pressurized relief chambers interconnected on the base material, wherein the independently pressurized relief chambers are configured in a geometric pattern that mitigates contact pressure between a support surface and a specific anatomic region of a user's body when pressure in the independently pressurized relief chambers is alternated and the specific anatomic region of the user's body is oriented over an epicenter of the geometric pattern. The plurality of elevated side support portions interconnected on the base material and configured to actively orient the specific anatomic region of the user's body laterally over the epicenter of the geometric pattern. The wedge portion interconnected on the base material and configured to actively orient the specific anatomic region of the user's body lengthwise over the epicenter of the geometric pattern.

In an embodiment, the wedge portion is configured to separate at least a portion of the user's lower extremities from the support surface.

In an embodiment, at least a portion of the user's lower extremities include the user's heels.

In an embodiment, the wedge portion further comprises a plurality of independently pressurized relief chambers interconnected on the wedge portion and configured in a second geometric pattern that mitigates contact pressure between the support surface and the user's lower extremities when pressure in the independently pressurized relief chambers interconnected on the wedge portion is alternated.

In an embodiment, the contact pressure mitigation support apparatus of claim further includes a wedge wrap portion interconnected on the base material and configured to wrap around the user's lower extremities to serve as a deep venous thrombosis prevention device.

In an embodiment, the contact pressure mitigation support apparatus further includes a wedge wrap portion interconnected on the wedge portion and configured to wrap around the user's lower extremities to serve as a deep venous thrombosis prevention device.

In an embodiment, the pressure-mitigating contact portion of the contact pressure-mitigation support apparatus is fitted to the user's body such that, when in use, the pressure-mitigating contact portion is completely covered by the user.

In an embodiment, the pressure-mitigating contact portion of the contact pressure-mitigation support apparatus is fitted to the user's body such that, when in use, the pressure-mitigating contact portion does not extend laterally beyond the user's body.

In an embodiment, the pressure-mitigating contact portion of the contact pressure-mitigation support apparatus is fitted to the user's body such that, when in use, the pressure-mitigating contact portion does not extend lengthwise beyond the user's body.

In an embodiment, the wedge portion interconnected on the base material is configurably detachable from the base material.

In an embodiment, the contact pressure mitigation support apparatus comprises an overlay.

In an embodiment, the geometric pattern includes a first independently pressurized relief chamber that intersects the epicenter of the geographic pattern, and second and third independently pressurized relief chambers that collectively encompass the first independently pressurized relief chamber.

In an embodiment, the pressure-mitigating contact portion of the contact pressure-mitigation support apparatus is fitted to the user's body such that when pressure in the independently pressurized relief chambers is alternated and the specific anatomic region of the user's body is oriented over the epicenter of the geometric pattern, the pressure-mitigating contact portion does not extend laterally or lengthwise beyond the user's body.

In an embodiment, the base material further comprises a first side having a first material disposed thereon and a second side having a second material disposed therein, and wherein the first material is configured for direct contact with the user's body and the second material is configured for direct contact with the support surface.

In an embodiment, the first material is breathable.

In an embodiment, the first material is more porous than the second material.

In an embodiment, the first material has a coefficient of friction that is greater than the coefficient of friction of the second material.

In an embodiment, the contact pressure between the support surface and the specific anatomic region of the patient's body is mitigated by alternating the pressure in one or more of the plurality of independently pressurized relief chambers.

In an embodiment, the elevated side support portions are configured to actively orient the specific anatomic region of the patient's body over the epicenter of the geometric pattern when pressurized.

In one embodiment, a contact pressure-mitigating support surface includes a support apparatus, a pressure-mitigating contact portion, a plurality of elevated side support portions, and a wedge portion. The pressure-mitigating contact portion including a plurality of independently pressurized relief chambers incorporated in the support apparatus and configured in a geometric pattern that mitigates contact pressure between the support apparatus and a specific anatomic region of a user's body when the specific anatomic region of the user's body is oriented over an epicenter of the geometric pattern. The plurality of elevated side support portions incorporated in the support apparatus and configured to actively orient the specific anatomic region of the user's body over the epicenter of the geometric pattern. The wedge portion incorporated in the support apparatus and configured to actively orient the specific anatomic region of the user's body lengthwise over the epicenter of the geometric pattern.

In an embodiment, the wedge portion is configured to isolate at least a portion of the user's lower extremities from the support surface.

In an embodiment, the contact pressure mitigation support surface of claim 20, further includes a plurality of independently pressurized relief chambers interconnected on the wedge portion and configured in a second geometric pattern that mitigates contact pressure between the support surface and the user's lower extremities when pressure in the independently pressurized relief chambers interconnected on the wedge portion is alternated.

In an embodiment, the contact pressure mitigation support surface of claim 20, further includes a wedge wrap portion incorporated in the support apparatus and configured to wrap around the user's lower extremities to serve as a deep venous thrombosis prevention device.

In an embodiment, the contact pressure mitigation support surface of claim 20, further includes one or more channel tubes incorporated in the support apparatus and configured to deliver pressure to the independently pressurized relief chambers.

In an embodiment, the contact pressure mitigation support surface of claim 20, further includes a pump incorporated in the support apparatus and configured to pressurize each of the independently pressurized relief chambers and a controller incorporated in the support apparatus and configured to regulate the pump.

In one embodiment, a contact pressure-mitigating system includes a contact pressure-mitigation support apparatus including a base material, a pressure-mitigating contact portion including a plurality of independently pressurized relief chambers interconnected on the base material, wherein the independently pressurized relief chambers are configured in a geometric pattern that mitigates contact pressure between a support surface and a specific anatomic region of a user's body when pressure in the independently pressurized relief chambers is alternated and the specific anatomic region of the user's body is oriented over an epicenter of the geometric pattern, a plurality of elevated side support portions interconnected on the base material and configured to actively orient the specific anatomic region of the user's body laterally over the epicenter of the geometric pattern, and a wedge portion interconnected on the base material and configured to actively orient the specific anatomic region of the user's body lengthwise over the epicenter of the geometric pattern. The contact pressure-mitigating system further includes a pump configured to pressurize each of the independently pressurized relief chambers and a controller configured to regulate pressure provided by the pump.

In an embodiment, the wedge portion is configured to separate at least a portion of the user's lower extremities from the support surface, and wherein the wedge portion further comprises a plurality of independently pressurized relief chambers interconnected on the wedge portion and configured in a second geometric pattern that mitigates contact pressure between the support surface and the user's lower extremities when pressure in the independently pressurized relief chambers interconnected on the wedge portion is alternated.

In an embodiment, the contact pressure-mitigation support apparatus further includes a wedge wrap portion interconnected on the base material and configured to wrap around the user's lower extremities to serve as a deep venous thrombosis prevention device.

In one embodiment, a partial body alternating contact pressure overlay device includes a base material, a pressure-mitigating contact portion, a plurality of elevated side support portions, a wedge portion, and a wedge wrap portion. The pressure-mitigating contact portion including a plurality of independently pressurized relief chambers interconnected on the base material, wherein the independently pressurized relief chambers are configured in a geometric pattern that mitigates contact pressure between a support surface and a specific anatomic region of a user's body when pressure in the independently pressurized relief chambers is alternated and the specific anatomic region of the user's body is oriented over an epicenter of the geometric pattern. The plurality of elevated side support portions interconnected on the base material and configured to actively orient the specific anatomic region of the user's body laterally over the epicenter of the geometric pattern. The wedge portion interconnected on the base material and configured to actively orient the specific anatomic region of the user's body lengthwise over the epicenter of the geometric pattern and the wedge wrap portion interconnected on the base material and configured to wrap around the user's lower extremities to serve as a deep venous thrombosis prevention device.

In an embodiment, the geometric pattern includes a first independently pressurized relief chamber that intersects the epicenter of the geographic pattern, and second and third independently pressurized relief chambers that collectively encompass the first independently pressurized relief chamber.

DETAILED DESCRIPTION

Figure 1:
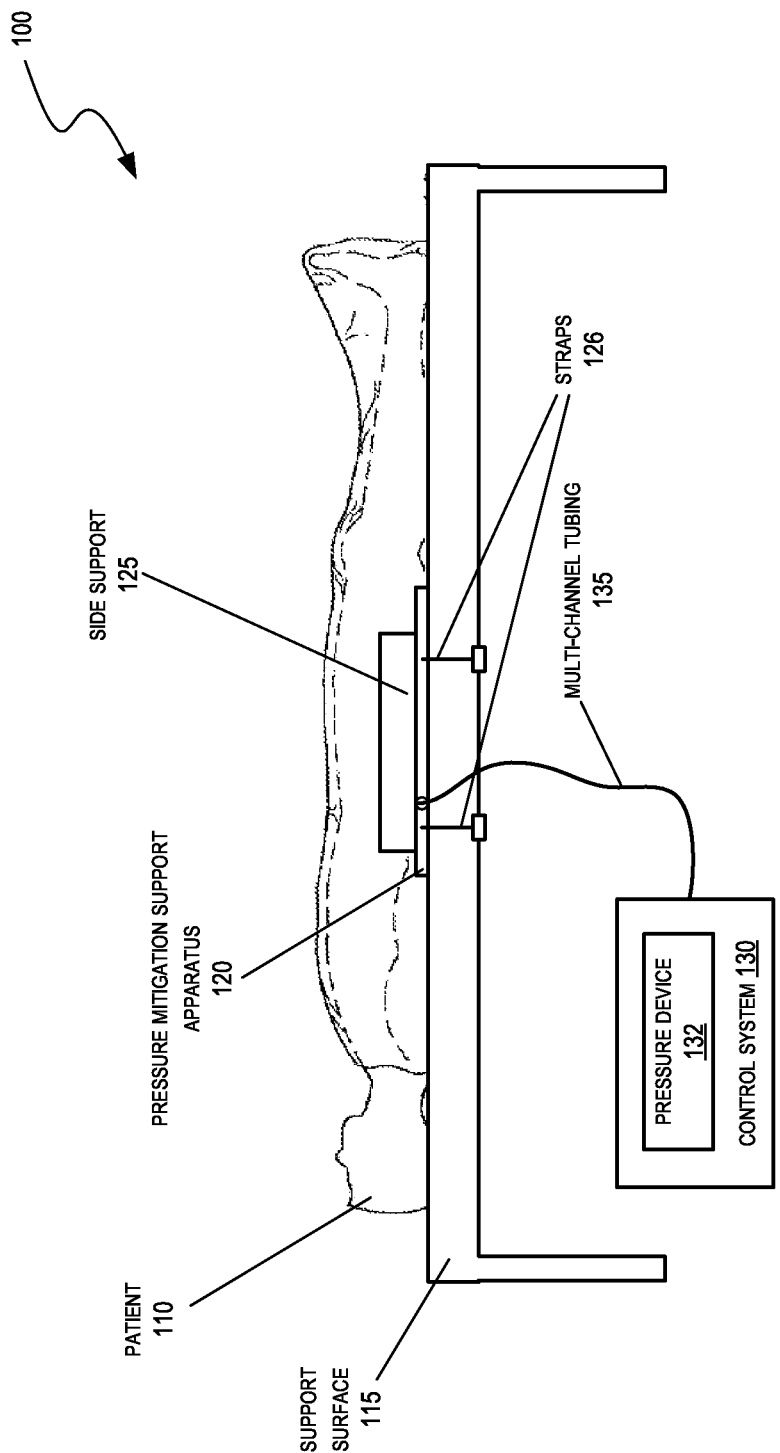
FIG. 1 depicts a side view of an example system for orienting a patient over an anatomy-specific pressure-mitigating contact surface on which the patient rests, according to an embodiment.

Embodiments of the present disclosure include examples of systems, methods, and apparatuses for the prevention and treatment of pressure ulcers. In particular, the ulcer prevention systems and/or apparatuses disclosed herein prevent or otherwise mitigate pressure ulcers by actively orienting a patient over an anatomy-specific pressure-mitigating contact surface on which the patient rests. A pressure-mitigating contact portion of the contact surface includes a plurality of independently pressurized chambers configured in a specific geometric pattern that is designed to mitigate contact pressure between a support surface (e.g., bed or chair) and a specific anatomic region of a patient's body when the specific anatomic region of the patient's body is oriented over an epicenter of the geometric pattern.

The following description and drawings are illustrative and are not to be construed as limiting. Numerous specific details are described to provide a thorough understanding of the disclosure. However, in certain instances, well-known or conventional details are not described in order to avoid obscuring the description. References to one or an embodiment in the present disclosure can be, but not necessarily are, references to the same embodiment; and, such references mean at least one of the embodiments.

Reference in this specification to "one embodiment" or "an embodiment" means that a particular feature, structure, or characteristic described in connection with the embodiment is included in at least one embodiment of the disclosure. The appearances of the phrase "in one embodiment" in various places in the specification are not necessarily all referring to the same embodiment, nor are separate or alternative embodiments mutually exclusive of other embodiments. Moreover, various features are described which may be exhibited by some embodiments and not by others. Similarly, various requirements are described which may be requirements for some embodiments but not other embodiments.

The terms used in this specification generally have their ordinary meanings in the art, within the context of the disclosure, and in the specific context where each term is used. Certain terms that are used to describe the disclosure are discussed below, or elsewhere in the specification, to provide additional guidance to the practitioner regarding the description of the disclosure. For convenience, certain terms may be highlighted, for example using italics and/or quotation marks. The use of highlighting has no influence on the scope and meaning of a term; the scope and meaning of a term is the same, in the same context, whether or not it is highlighted. It will be appreciated that same thing can be said in more than one way.

Consequently, alternative language and synonyms may be used for any one or more of the terms discussed herein, nor is any special significance to be placed upon whether or not a term is elaborated or discussed herein. Synonyms for certain terms are provided. A recital of one or more synonyms does not exclude the use of other synonyms. The use of examples anywhere in this specification including examples of any terms discussed herein is illustrative only, and is not intended to further limit the scope and meaning of the disclosure or of any exemplified term. Likewise, the disclosure is not limited to various embodiments given in this specification.

Without intent to further limit the scope of the disclosure, examples of instruments, apparatus, methods and their related results according to the embodiments of the present disclosure are given below. Note that titles or subtitles may be used in the examples for convenience of a reader, which in no way should limit the scope of the disclosure. Unless otherwise defined, all technical and scientific terms used herein have the same meaning as commonly understood by one of ordinary skill in the art to which this disclosure pertains. In the case of conflict, the present document, including definitions, will control.

In one embodiment, the ulcer prevention systems and/or apparatuses control pressure beneath specific anatomic locations of the patient for specific durations in order to maximize blood flow and reduce pressure over bony prominences in an effort to reduce the incidence of pressure ulcers. Thus, the ulcer prevention systems and/or apparatuses make it possible to increase and decrease the pressure beneath a patient at specific locations for set periods of time in order to maximize the potential therapeutic benefits of the a therapeutic surface.

In one embodiment, the ulcer prevention systems and/or apparatuses are specifically designed for mitigating pressure and/or otherwise preventing pressure ulcers in the sacral area or region of the human anatomy. This is unlike prior art surfaces or overlays that are typically placed beneath the entire length of the patient and do not function based on being uniquely oriented beneath a specific location (or anatomic region) of the patient.

In one embodiment, the geometric pattern is designed and/or shaped according to general human anatomy and/or the individual patient's specific anatomy. For example, if the ulcer prevention systems and/or apparatuses are designed to mitigate contact pressure between a support surface and the patient's sacral region then the independently pressurized chambers are designed in specific shapes to fit to the patient's pelvic bones, the gluteus muscles, and/or the sacral arties. In one embodiment, the geometric pattern is symmetric and non-repeating in nature.

In one embodiment, the device's patient contact portion is designed to actively orient the patient over the support surface portion in a way that allows an apparatus to "know" for the first time the location of the patient on that device. The apparatus is designed to take advantage of this knowledge regarding the location of the patient to more effectively mitigate and systematically rotate the damaging pressure that leads to the formation of pressure ulcers.

In one embodiment, the apparatuses described herein comprise mattress overlay devices. The described overly devices differ from the prior art mattress overlays that cover the full surface of the bed. Further, the prior art mattress overlays typically have a repeating pattern throughout and allow a patient to freely move about over the entire surface of the bed. Conversely, the apparatuses described herein are anatomy-specific and may only be the size of the patient's anatomy that makes contact with the apparatus. Accordingly, the disclosed systems, methods, and apparatuses take advantage of the inherent knowledge of the patient's location on the anatomy-specific pressure-mitigating contact surface to systematically rotate and/or otherwise alternate the damaging pressure that leads to the formation of pressure.

In one embodiment, the patient can be actively oriented over an anatomy-specific pressure-mitigating contact surface by controlling the spatial relationship between the patient and the contact surface through the use of one or more side support portions. In some embodiments, the side support portions may be inflatable. In other embodiments, the side support portions are fixed. In the former case, the side support portions may be independently inflated with any appropriate gas or liquid. The inflation of the side support portions is independent of the pressurized relief chambers on the pressure-mitigating contact portion. In some embodiments, the side support portions may be inflated independent of each other in order to properly orient the patient. This can be based on the actual pressure in a side support portion versus an expected pressure in that side support portion as determined by a control device. Alternatively or additionally, one or more sensors can be built into the side support portions that identify discrepancies in the ideal position of the patient on the anatomy-specific pressure-mitigating contact surface and attempt to adjust the patient accordingly (e.g., by independently adjusting the pressure in the side support portions).

In one embodiment, the pressure in the side support portions is fixed. In this case, the fixed side support portions may be fixed using a liquid, a gas, and/or a solid. In the case where a solid is used, Styrofoam, and/or any "cushion like" materials can be utilized. The side support portions may be elevated in height above the anatomy-specific pressure-mitigating contact surface in order to prevent a patient from lateral movement (i.e., movement along the x-axis). For example, the side support portions may be elevated, when inflated, two to three inches in vertical height above the average surface height of the pressure-mitigating contact portion.

Further, to prevent movement along the y-axis the anatomy-specific pressure-mitigating contact surface may be designed such that a specific portion of the contact surface is aligned over the surface of a V formed in a patient's hospital bed. In one embodiment, the side support portions may be attached to the sides of a pressure-mitigating contact portion. In one embodiment, the side support portions may be configured with a recess configured to accommodate a patient's elbow. The recess that accommodates the patient's elbow results in a more comfortable device that offloads pressure over the elbow of the patient.

In one embodiment, the design of the ulcer prevention systems and/or apparatuses disclosed herein take into account and/or control for various factors that influence functionality and/or effectiveness of the ulcer prevention systems and/or apparatuses. For example, the systems and/or apparatuses may take time, space, patient weight, patient position, real-time interface pressure, existing conditions (e.g., existing pressure ulcers), and/or human anatomy into account in the prevention of pressure ulcers.

In one embodiment, the systems and/or apparatuses may be employed as a mattress overlay. For example, the overlay device or apparatus could be deployed on any mattress or chair. Alternatively or additionally, the systems and/or apparatuses may be incorporated into the design of a mattress.

In one embodiment, the surface area of the pressure relief surface is designed to match (or be less than) the size of the patient's surface anatomy in the region of contact made between the patient's anatomic region and the device. For example, the size of the pressure relief surface may be the size of the patient's surface anatomy in the region of contact made between the patient's sacral region and the pressure mitigation support apparatus. Further, the pressure relief surface may be contoured to fit the surface topography of the patient's surface anatomy in the region of contact made between the patient's sacral region and the pressure mitigation support apparatus. The internal anatomy is considered in the pattern—not the height—of the relief chamber design.

In one embodiment, the pressure relief apparatus is designed such that no portion of the independently pressurized relief chambers of the surface area of the pressure relief surface in contact with the patient is left uncovered by the patient. That is, the independently pressurized relief chambers in contact with the patient can be smaller than or equal to but not larger than the area of contact with the patient. This feature improves performance of the pressure relief apparatuses described herein. Conversely, with prior art standard alternating pressure overlays, the pressure relieving air cells are much larger than the contact area with the patient and therefore the air cells are only partially covered by of the patient. Thus, with prior art designs, the uncovered portions of the pressure relieving air cells act as a reservoir "sink" for the inflated air and minimize the lifting capabilities of these surfaces that are needed to create areas of low pressure fundamental to the optimal functioning of such a device.

In one embodiment, the independently pressurized relief chambers of the pressure relief apparatus are unique in that the entirety of the surface area of the independently pressurized relief chambers are in contact with the patient such that no portion of the independently pressurized relief chambers is left uncovered by the user. Therefore, in this embodiment, the individual independently pressurized relief chambers of the pressure relief apparatus can be smaller than or equal to but not larger than the area of contact with the patient. This feature can improve performance of the pressure relief apparatus. In the case of prior art standard alternating pressure overlays, the pressure relieving air cells are much larger than the contact area with the patient and therefore the air cells are only partially covered by of the patient. Thus, with prior art designs, the uncovered portions of the pressure relieving air cells act as a reservoir "sink" for the inflated air and minimize the lifting capabilities of these surfaces that are needed to create areas of low pressure fundamental to the optimal functioning of such a device.

In one embodiment, the systems and/or apparatuses can be employed as a mattress overlay and/or incorporated into the design of a mattress itself. The overlay can be deployed on any mattress or chair. The design of the pressure mitigation surface portion of the overlay portion of the device takes into account multiple factors. These factors include patient comfort, patient anatomy, patient position (seated, flat, 30 degrees head up), and anatomic locations with a propensity to develop pressure ulceration.

It is appreciated that the term "patient" as used herein can include any individuals, users or persons that are in bed for prolonged periods of time and thus susceptible to pressure ulcers.

FIG. 1 depicts a side view of an example system 100 for orienting a patient over an anatomy-specific pressure-mitigating contact surface on which the patient rests, according to an embodiment. The example system 100 includes a patient 110, a support surface 115, a pressure mitigation support apparatus 120 and a control device 130. A more detailed example of a specific pressure mitigation support apparatus (e.g., partial body alternating contact pressure mattress overlay device) is shown and discussed in greater detail with respect to FIG. 2.

In the example of FIG. 1, the pressure mitigation support apparatus 120 is comprised of two elevated side support portions 125, a pressure-mitigating contact portion (shown in FIG. 2), and straps 126. The pressure-mitigating contact portion includes a plurality of independently pressurized relief chambers interconnected on a base material. As described herein, the independently pressurized relief chambers are configured in a geometric pattern that mitigates contact pressure between the support surface 115 and a specific anatomic region of a patient's body when the specific anatomic region of the patient's body is oriented over an epicenter of the geometric pattern. The support surface 115 may be a hospital bed and/or mattress.

The elevated side support portions 125 are configured to actively orient the specific anatomic region of the patient's body over the epicenter of the geometric pattern. As shown, the specific anatomic region of the patient's body is the sacral region. However, it is appreciated that the specific anatomic region can be any specific region of the patient's body that is susceptible to pressure ulcers. The side support portions 125 are configured so as to be ergonomically correct. For example, the side support portions 125 may be configured with a recess to accommodate the patient's elbows in some embodiments resulting in a more comfortable apparatus that off loads pressure over the elbow of the patient.

The elevated side support portions 125 can be significantly larger in size as compared to the size of the pressure relief surface air cells. As a result, the elevated side support portions 125 create a barrier that keeps a patient from moving laterally or sideways off of the anatomy-specific pressure-mitigating contact surface. In one embodiment, the elevated side support portions 125 may be on average at least 2-3 inches taller in vertical height after inflation as compared to the average height of the inflated (or pressurized) pressure-mitigating contact portion. Because the elevated side support portions 125 are larger and do not go underneath the patient, but instead straddle the sides of the patient, the elevated side support portions 125 act to hold and position the patient on top of the anatomy-specific pressure-mitigating contact surface.

The straps 126 are configured to secure the pressure mitigation support apparatus to the support surface.

In one embodiment, inner side walls of the elevated side support portions 125, on initial inflation of higher pressure, form a firm surface at a steep angle of orientation with respect to the patient on the pressure mitigation support apparatus 120. For example, the inner side walls may be on a plane of 115 degrees plus or minus 25 degrees from the plane of the pressure mitigation support apparatus 120. These steep inner side walls create a steeply angled side wall down which the patient, when positioned inappropriately off to one side or another, will slide down toward an epicenter of a geometric pattern formed on the pressure mitigation support apparatus 120. Thus, inflation or pressurization of the elevated side support portions 125 actively forces the patient into a position ideal for the mitigation of pressure by orienting the user in the correct position over the pressure mitigation support apparatus 120. As a result, the patient's anatomy will be correctly aligned with respect to the x-axis.

Once the initial inflation cycle has finished and the user is properly positioned, the internal pressures of the elevated side support portions 125 may decrease to a lower pressure to increase comfort and prevent excessive force against the lateral aspect of the patient. Ideally, a caregiver of the patient will be present during the initial positioning of the patient over the pressure mitigation support apparatus 120 to ensure proper positioning of the patient by the elevated side support portions 125.

In one embodiment, the elevated side support portions 125 comprise steeply angled side walls. For example, the walls may be angled such that the inner aspect of the elevated side support portions 125 which contact the user on the lateral aspects of each hip/thigh region simultaneously will form an obtuse angle of between 90 to 145 degrees with respect to the plane of the pressure mitigation support apparatus 120 (i.e., a pressure-mitigating contact portion). The elevated side support portions 125 may be connected by pressure channels (e.g., air channels).

In one embodiment, the elevated side support portions 125 are inflated and deflated in series together. Thus, like the independently pressurized relief chambers, the air pressure in the elevated side support portions 125 can be controlled by the control device 130. Alternatively or additionally, each side support portion of the elevated side support portions 125 can be controlled by a unique control device and/or pump within the pump housing. The pressures within the elevated side support portions 125 can be determined based on pre-set parameters of the individual pump cycle as determined on an individual patient specific basis (e.g., individual parameters based on the weight, existing pressure ulcers, and/or position of the patient).

In one embodiment, there can be one or more air (or pressure) channels (not shown) between the elevated side support portions 125. In some cases, the air channels can be redundant. Redundancy of air channels allows for even distribution of air (or other pressure) between the elevated side support portions 125. For example, one air channel may traverse the outside (or perimeter) of the pressure mitigation support apparatus 120 to the top of the apparatus while a second air channel traverse the outside of the pressure mitigation support apparatus 120 a lower edge of the apparatus. This configuration or arrangement creates a closed loop circle around the pressure mitigation support apparatus 120 which allows air to pass unobstructed from the pump into a first one of the elevated side support portions 125 through the connecting air channels and into a second one of the elevated side support portions 125 without the weight of the patient blocking both channels simultaneously as this is physically improbable with the redundant configuration described herein.

In one embodiment, the pressure channels can flare out slightly at the point of entry into the elevated side support portions 125 so as to reduce the likelihood of kinking or otherwise disturbing the inflation and/or pressurization of the pressure channels.

In one embodiment, the pressure mitigation support apparatus 120 can have an additional elevated side support portion 125 that is positioned between the legs of a patient along the lower aspect of the pressure mitigation support apparatus 120 (not shown). This additional elevated side support portion 125 can prevent a patient from migration toward the foot of the bed in the y-axis.

In one embodiment, the elevated side support portions 125 function much like the side arms of a chair which has a seat portion that is the same size as the "seat" of the user (e.g., a chair that is too small for a user) These side arms allow only a small lateral position shift of the user. As is the case with the pressure mitigation support apparatus 120, this minimal lateral motion is not great enough to allow the user to displace their location off of the pressure mitigation support apparatus 120 to a degree that will render the pressure relief characteristics less effective.

The control system 130 is configured to regulate the pressure of each of the independently pressurized relief chambers via a pressure device 132 (e.g., air pump) and multi-channel tubing 135. For example, the independently pressurized relief chambers may be controlled in a specific pattern to preserve blood flow and reduce contact pressure when inflated (pressurized) and deflated (depressurized) in a coordinated fashion that is controlled by the control device 130. The multi-channel tubing 135 connects the pressure mitigation support apparatus 120 with the air pump control system 130. One or more connectors (not shown) may be used to make these connections.

The control system 130 is configured to be programmed by a patient, healthcare personnel, the patient, etc. In one embodiment, the control system 130 can be programmed on a patient-specific basis to manage and mitigate pressure on one or more existing pressure ulcers that are currently present on a patient in a specific anatomic location. As the geometry of the design is specific to the patient's anatomy, the location of the pressure ulcer on the patient can be entered into the computer controlled pump and the ideal pressure time cycle optimized for healing the ulcer in that specified anatomic location. For example, if a patient has an ulcer in the typical location over the sacral bone centrally, the cycle will preferentially drop the pressures in this location and shorten the duration of pressure delivered to this location in order to promote healing of the ulcer. Similarly, if the ulceration is located over a specific ischial tuberosity, right or left, the pressure can be preferentially relieved in this location as the independently pressurized chambers are specifically designed to fit the underlying anatomy and each region of concern is able to be controlled specifically.

In one embodiment, the multi-channel tubing 135 comprises multi-lumen tubing to control pressure at different chambers of the plurality of independently pressurized chambers. Multi Lumen tubing has multiple channels running through its profile. Multi Lumen tubing has a variable Outer Diameter (OD), numerous custom Inner Diameters (ID's), and various wall thicknesses. The tubing can be in a number shapes; circular, oval, triangular, square, crescent, etc.

In one embodiment, the control system 130 may comprise a computer-controlled multi-channel air pump. The control system 130 may have a number of programmable settings and memory to remember preferences. Further, in some embodiments, the control system 130 can control pressure beneath one or more specific anatomic location(s) for specified durations in order to maximize blood flow and reduce pressure. The specified durations can be programmable. For example, the control system 130 can control the pressure in each of the individual pressurized relief chambers of the pressure mitigation support apparatus 120 such that the pressure in any chamber changes or is modified after a specified period of time. In this way, no part of the patient's body is left in contact with the pressure mitigation support apparatus 120 for more than a period of time. The period of time is programmable and may be based on pre-programmed settings or customizable by the patient and/or a health care professional.

Unlike some alternating pressure support surfaces, the adjustable side walls 125 fix the relationship between the patient and the pressure mitigation support apparatus 120. As a result the pressure mitigation support apparatus 120 can reliably reduce pressure in a concerted or consistent fashion for any specific region of the patient's body in jeopardy of developing a pressure ulcer because the patient is not free to move about over the pressure mitigation support apparatus 120. Further, unlike products with side support surfaces such as, for example, supports to keep patients from falling off a large overlay support surface (i.e., a mattress overlay) or the supports on a typical hospital bed, the side supports 125 are customizable to the patient. For example, the side walls 125 may be inflatable (pressurized) to fit to the patient and keep the patient in the correct position (i.e., keep the anatomic region of the patient's body oriented over an epicenter of the geometric pattern). The pressure mitigation support apparatus 120 presented herein is designed with a geometry that requires the patient be properly held in position on the surface in order for the design to effectively mitigate the pressure beneath the patient and maximize blood flow to the tissues at risk for ulceration.

In one embodiment, the side supports 125 will contact the patient gently on the lateral aspect of both hips simultaneously in order to actively orient the patient in the correct orientation on the surface. The pressure mitigation support apparatus 120 can be customized specifically to each individual patient in order to be effective at pressure ulcer reduction. As will be appreciated, this design is quite different from the support surfaces that utilize side walls as a safety barrier to prevent patients from moving off or falling off the surface support as the patient is free to move about over these surfaces laterally between the sidewalls that are typically as wide apart as a standard hospital bed. These current products do not require the person to be in a precise location on the surface as opposed to the patient-orienting surface described here.

Being anatomy (or location) specific beneath the patient, allows the apparatus to evenly distribute and rotate pressure from one known location to another ensuring that no one area is under the damaging effects of constant pressure for a prolonged period of time that could lead to cell death from ischemia that leads to tissue breakdown and pressure ulcer formation. Prior art support surfaces which allow a patient to move freely over the support surface cannot reliably rotate pressure from a specific area to another and therefore are limited in their ability to prevent pressure ulceration as compared to the systems and apparatuses described herein.

Figure 3:
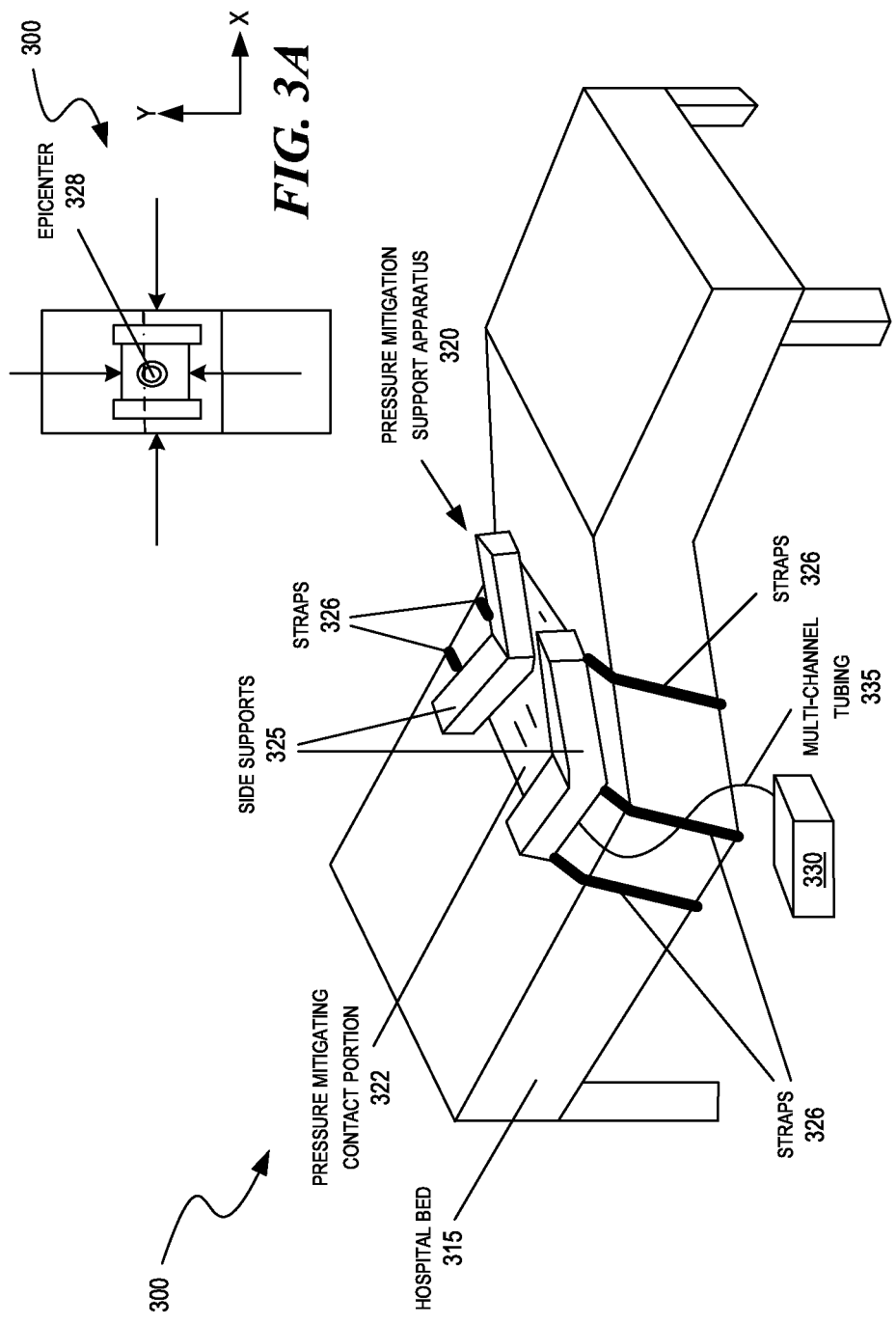
FIG. 3A and FIG. 3B depict top and side views, respectively, of an example system for orienting a patient over an anatomy-specific pressure-mitigating support surface on which a patient rests, according to an embodiment.

Ideally, patients are positioned head up at 30 degrees in bed to prevent aspiration pneumonia and to optimally offload the patient's weight off of the sacrum and ischial tuberosities. This is also the ideal bed position to ensure optimal function of the apparatuses disclosed herein. However, in the event that a patient is positioned flat in bed at 0 degrees as shown is the case of the intubated, anesthetized and hypotensive ICU patient (and as shown in FIG. 1), it will be necessary to confirm ideal patient position over the device without the benefit of y-axis orientation control achieved by placing the bed at 30 degrees head up (discussed in greater detail with reference to FIG. 3).

In one embodiment X- and/or Y-axis orientation control can be alternatively or additionally achieved through the use of a radio frequency (RF) antenna device. For example, as an additional measure to confirm patient location over the epicenter of our device, an RF antenna can be incorporated into the pressure-relieving surface. A thin flexible RFID tag/label may be placed on the patient's sacrum using a biologic dressing material. When in the proper orientation, the RFID tag will be detected by the antennae and a signal light and sound will confirm the correct position without needing to look beneath the patient and inspect correct location by direct vision. The indicator signal will display the correct direction in which to move the patient should reorientation be required by the staff to ensure the immobile patient is correctly positioned over the device to maximize pressure redistribution and pressure rotation/relocation.

Figure 2:
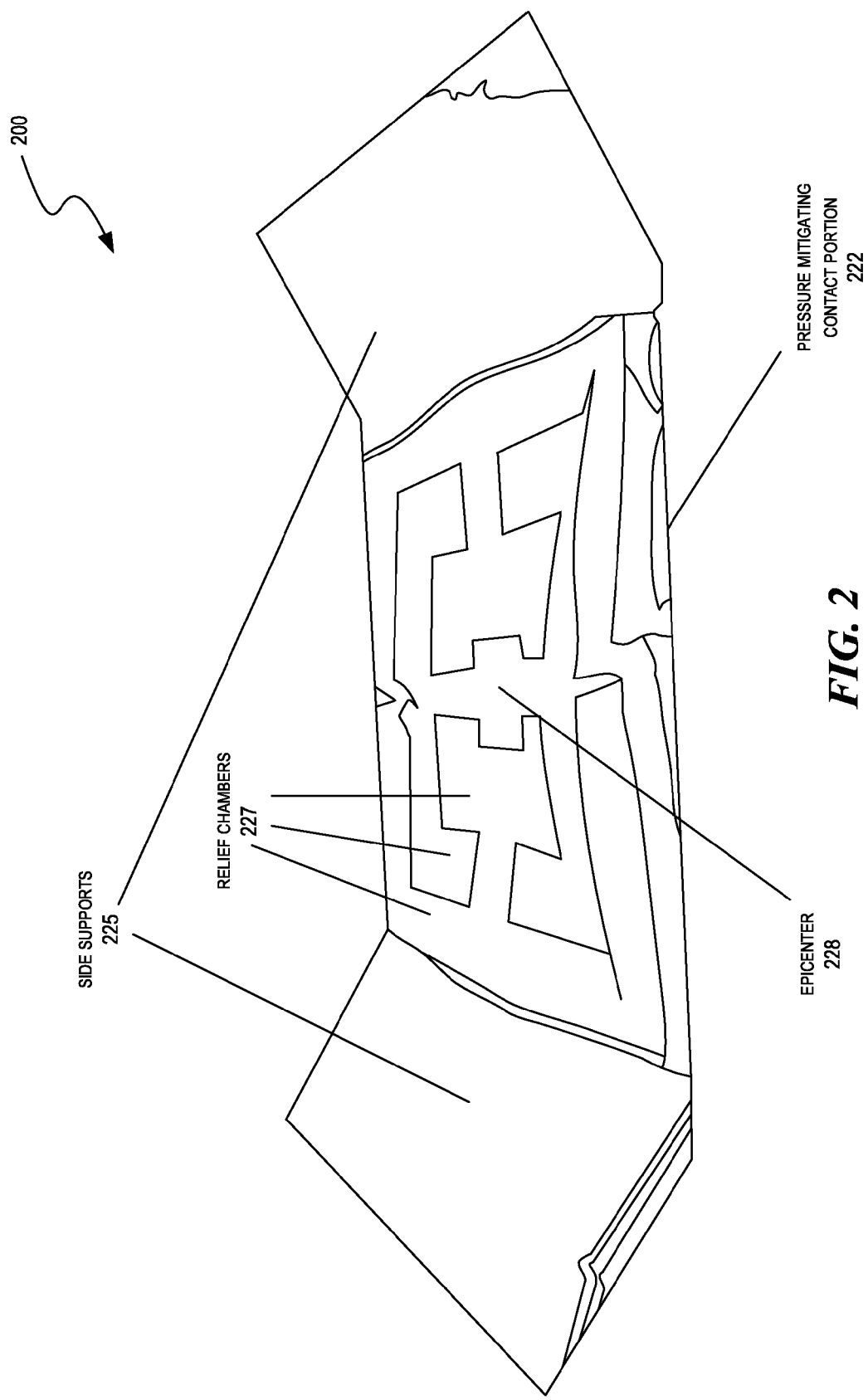
FIG. 2 depicts an example pressure mitigation support apparatus, according to an embodiment.

FIG. 2 depicts an example pressure mitigation support apparatus 200, according to an embodiment. The pressure mitigation support apparatus 200 includes side supports 225 and a pressure-mitigating contact portion 222. The pressure-mitigating contact portion 222 includes a plurality of independently pressurized relief chambers 227. The independently pressurized relief chambers 227 are configured in a specific geometric pattern that mitigates contact pressure between a support surface and a specific anatomic region of the patient's body when the specific anatomic region of the patient's body is oriented over an epicenter of the geometric pattern.

As shown in the example of FIG. 2, the epicenter may be a central point of the pressure mitigation support apparatus, however the epicenter need not be the central point of the apparatus. For example, the epicenter may not be the central point if the pressure mitigation support apparatus is not symmetric (or even if it is). In some embodiments, the epicenter is a portion of the device that is specifically designed to match up with an epicenter of the specific anatomic region of the patient's body (e.g., the sacral bone when the specific anatomic region is the sacral region). In one or more embodiments, the epicenter will be marked so that a patient and/or a caregiver (e.g., nurse) can easily identify the epicenter of the apparatus.

In this example, the pressure mitigation support apparatus 200 includes a plurality of independently pressurized relief chambers 227 that are configured in a specific "C-shaped" geometric pattern that effectively mitigates and/or otherwise relieves contact pressure between a support surface and a sacral region of a patient's body when the pressure in the plurality of independently pressured relief chambers 227 is alternated. The anatomy specific "C-shaped" geometric design allows the geometric pattern to properly align with the patient's anatomy resulting in superior redistribution and relocation of pressure as compared to prior art support surfaces.

The geometric pattern(s) described herein are specifically designed to coincide with the internal anatomy of the sacral region. For example, the geometric pattern of independently pressurized relief chambers 227 conforms to a shape based on the internal anatomy (muscle, bone, vessel) in order to maximize the pressure-relieving properties of the apparatus. As a result, pressure relief can be provided in specific areas of the sacral region that are most prone to ulcer formation, namely over the bony prominences—the sacrum and ischial tuberosities. The pattern of the apparatus is therefore symmetric and non-repeating in nature. This is different from prior art support surfaces that typically employ repeating patterns over a large surface area of an entire bed mattress. The functionality of these prior art surfaces do not require knowledge of the location of a patient. That is, with prior art surfaces there is no benefit for the patient being in one location verses another. Accordingly, the prior art surfaces are less effective and less accurate than the systems and/or apparatuses disclosed herein.

In the example of FIG. 2, the geometric pattern illustrates two lateral relief chambers forming "C" shapes facing each other around a central circular relief chamber which is the size of the sacral bone and positioned directly over the sacral bone. The central circular relief chamber is designed to fit the area of skin just at the top of the gluteal fold that overlies the sacral bony prominence which is the area at greatest risk for pressure ulcer formation.

In addition to the ability to directly relieving central pressure, the device is designed to intermittently relieve pressure just lateral to this central area. It is in this lateral region that the blood supply to the central region is located. The major blood supply via a named artery to the skin overlying the central sacral area runs in a course from deep within the pelvis around the lateral aspect of the sacral bone and travels to the skin overlying the sacrum centrally. Lateral pressure directly beneath the C shape regions which overlies the feeding arterial blood supply to the central sacral region will lead to ulceration centrally over the sacral bony prominence. The C shapes are located directly over the superior gluteal arteries, the vascular blood supply to the skin overlying the sacral bone.

A right and left superior gluteal artery run beneath the right and left C shapes respectively. By deflating the relief chamber that comprises the right C shape while the central air cell and the left C shaped relief chamber remain inflated, the pressure over the right superior gluteal artery is relieved and blood flow is optimized through the right superior gluteal artery to skin overlying the central area over the sacral bone. Similarly, pressure can be relieved over the left superior gluteal artery by performing a similar process with respect to the C-shaped air cell over the left superior gluteal artery. Pressure is rotated from one area to another as a result. The harmful effects of constant pressure in one location for a prolonged period of time which can lead to pressure ulcer formation are therefore avoided. These air cells are intertwined so that any individual air cell may be deflated and the other air cells that remain inflated will support the area defined by the now un-inflated air cell such that an area of low pressure is created in the area beneath the un-inflated air cell.

In one embodiment, the specific pressure mitigation support apparatus 200 may be a partial body alternating contact pressure mattress overlay device as shown and discussed in greater detail with respect to FIG. 3A and FIG. 3B. The pressure mitigation support apparatus 200 may be the pressure mitigation support apparatus 120 of FIG. 1; although alternative configurations are possible.

In the example of FIG. 2, the side supports 225 control the spatial relationship between the patient and the pressure-mitigating contact portion 222. As discussed, the geometric pattern of the pressure-mitigating contact portion 222 is designed to reduce constant pressure on the patient in the same place. In one embodiment, the side supports 225 may not be inflatable but fixed. In one embodiment, side supports 225 are disposed on each side of the support surface 200 to support patients of variable hip width. Further, in some embodiments, the side supports 225 may be decreasing in width from the outermost wall to the innermost wall. It is appreciated that a geometric pattern is shown for simplicity. The pressure-mitigating contact portion 222 may include a variety of different patterns and/or designs and sizes. Further, it is appreciated that the specific pressure mitigation support apparatus 200 can be designed to reduce pressure for specific regions or portions of a patient's body and/or for a patient's entire body in some instances.

A control system such as, for example, the control system 130 of FIG. 1 individually controls the pressure in each of the independently pressurized relief chambers. The pressure and length of time each air cell is at a specific pressure will be determined by an algorithm within the software program. In order to maximize the efficacy of the system, the specific pressures and timing cycles that will be utilized are patient-specific. The specific program (time/pressure cycle) specified for an individual patient may be determined by the specific patient's characteristics and/or factors that are entered into the pump controller program. This data is used to call for the optimal program for that patient. Possible characteristics and/or factors can include, but are not limited to, the patient's weight, the type of surface upon which the apparatus or overlay rests (e.g., bed, stretcher, air mattress, etc.), the patient position (flat in bed, bed at 30 degrees, bed at 45 degrees, bed at 90 degrees, sitting in chair, etc.), and/or the location of preexisting pressure ulcers. These characteristics and/or factors may be used to determine the pressure for the independently pressurized relief chambers over a period of time (e.g., the alternating pressure or the pressures needed to effectively redistribute and relocate pressure within a specific anatomic area).

In one embodiment, real-time (or near real-time) feedback from the independently pressurized relief chambers will allow the pump to adjust the pressure within each relief chamber towards the desired set pressure for each air cell at each phase of the cycle. Each relief chamber may be set to a specific pressure for a specific length of time. The cycles of each chamber will be coordinated with respect to all other chambers creating a coordination of inflations and deflations of the entire group of pressure relief chambers to maximize pressure redistribution and relief within the apparatus. It is appreciated that there are a finite number of cycle patterns that can achieve the desired result based on the physical constraints dictated by the human anatomy, the size of the sacral area, and the size that the air cells need to be in order to be effective at pressure relief yet comfortable and not prone to mal-align the long axis of the patient's spine if they are too tall in height.

The physiologic pressure around 32 mmHg is the ideal threshold below which pressure ulceration is less likely to occur. Given this ideal pressure target of 32 mmHg, the apparatus includes an ideal size of 2-3 inches for the pressure relief chambers in a partial body overlay that will create the required wall tension of the surface of these air cells to effectively redistribute high pressure points without causing mal-alignment of the long axis of the patient's spine. Additionally, in some embodiments, the difference in height between adjacent pressure relief chambers is not more than 1 inch in vertical height after inflation so as not to create a surface that is uncomfortable to the patient.

The ideal internal pressures that are optimal in conjunction with the identified ideal shapes of the pressure-relieving portion of the device or apparatus, namely, given the shape and design of the pressure relief surface (or pressure-mitigating contact portion), using pressures within the central pressure relief chamber that are on average 10 mmHg higher than the two lateral pressure relief chambers will produce, include optimal redistribution of interface pressure between the patient and the device.

In one embodiment, the pressure mitigation support apparatus 200 may be constructed of various materials. For example, material used in construction of the inflatable or patient contact portion of the pressure mitigation support apparatus 200 may be determined by the nature of the contact. If the pressure mitigation support apparatus 200 is in direct contact with skin a soft, low sheer, breathable fabric is ideal. This fabric will have an impervious lining like, for example, polyurethane, etc. that is air tight and used to create the air tight chambers. The materials may be reusable and sterilizable. Conversely, if the pressure mitigation support apparatus 200 is underneath a protective cover or bed sheet, then the inflatable device can be made of an impervious flexible material like polyurethane. This is ideal for a multi-patient patient as it is easily washable and sterilized.

FIG. 3A and FIG. 3B depict top and side views, respectively, of an example system 300 for orienting a patient over an anatomy-specific pressure-mitigating support surface 320 on which a patient (not shown) rests, according to an embodiment. In this example, the anatomy-specific pressure-mitigating support surface 320 is used in conjunction with a typical hospital bed 315 (i.e., support surface) to control the spatial relationship between the patient and the hospital bed. A control system 330 alternates pressure in the chambers of the anatomy-specific pressure mitigating support surface 320. The control system 330 may be the control system 130 of FIG. 1, although alternative configurations are possible.

More specifically, in the examples of FIG. 3A and FIG. 3B the support device 320 is placed on or otherwise secured to a standard hospital bed 315 that can maintain a 30 degree incline position. The epicenter of the device 328 is aligned over the break in the bed so that when a patient is seated on the device the side supports 325 keep the person centered laterally (e.g., along the x-axis or from side to side). In this configuration, the bed is in a 30 degree "V" shape position that will keep the person from moving toward the head or foot of the bed. This creates a centering of the patient over the surface in both the east-west (between the side walls) and north-south (between the head and leg elevations) directions.

The epicenter 328 of the pressure relieving surface of the apparatus is designed to contact the sacrum of the patient at the top of the gluteal fold. This is the area of greatest incidence of pressure ulceration in bed bound individuals. The apparatus is specifically and uniquely shaped to protect this portion of the patient anatomy as it represents the center of the pressure relief surface around which the design is constructed. Conversely, as previously discussed, the repeating patterns of prior art surface designs at are not anatomy specific. The epicenter 328 is designed to be placed and fixed on a support surface (e.g., hospital bed) such that the epicenter 328 is located and/or otherwise oriented over the break (or "V") in the bed.

In one embodiment, the epicenter 328 of the apparatus is readily identified by its visual characteristics and marked by a central 0.5 inch weld at the very center of the pattern. This central half inch circle is visually aligned with the joint in the bed frame that acts as the hinge point for flexing or breaking of the bed into the 30 degree position.

In one example of installation on bed, the bed is first inspected for the joint or pivot point. The overlay device or apparatus is then placed on the bed so that the central point or 0.5 inch circular weld within the central 4×4 inch relief chamber at the epicenter 328 of the overlay is directly over this joint or hinge point in the bed. Lastly, the overlay is attached to the bed frame at all four corner of the overlay using the one or more straps 326. In one embodiment, the straps 326 may be 1 inch Velcro straps; however any straps that can hold overlay to the bed can be used. The overlay can be placed directly on the mattress and covered by a fitted sheet or it can be attached to the bed over the fitted sheet. A protective sleeve can be places over the overlay to protect it and reduce cleaning requirements.

Once a patient is placed on the bed over the overlay device or apparatus, the patient is in a location known to or actively oriented by the device or apparatus and the control system can then inflate (pressurize) and deflate (depressurize) the pressure relief chambers of the relieving portion of the overlay in a preprogrammed cycle for specific time/pressure values to optimize the pressure-relieving capabilities of the system. The pressure and timing cycles are also unique and specific to the design of the system. The pressure and timing cycles may take into account the weight of the patient, the position of the bed, and/or the type of surface on which the overlay is resting, etc. The pressures used by the control system may be calculated to be the minimal pressures needed to achieve even redistribution of high pressure. Interface pressure may be determined by the patient's weight and body position. The greater the weight, the greater the downward pressure of the patient on the overlay, and thus the greater the internal pressure will need to be in order to lift the patient off the underlying mattress in order to effect the redistribution of pressure from high points to low points. This data may be programmed into the controller by the healthcare team prior to use and is specific for each patient.

In one embodiment, the surface area of the pressure-mitigating contact portion 322 (e.g., or pressure relief surface) of the pressure mitigation support apparatus 320 is designed to match the size of the patient's anatomy in the region of contact made between the patient's sacral region and the apparatus. Thus, the size of the pressure-mitigating contact portion 322 is the size of the patient's surface anatomy between the patient's lower back to the mid thigh region (i.e., the sacral region). The sacral region is typically a 20×20 square inch area for the standard adult male of 75 Kg. In some embodiments, the pressure mitigation support apparatus 320 may be size matched to the patient. For example, the pressure mitigation support apparatus 320 may come in various sizes such as small, medium, large, extra-large, etc. The sizes may thus range from a 12×12 square inch area to a 35×35 (or greater) square inch area.

The pressure-mitigating contact portion 322 is also patient size specific and designed to mirror the size of the patient. Thus, the device or apparatus can have several sizes depending on the patient's anatomy (e.g., small, medium, large, extra-large, etc.). The device or apparatus is designed so that when sized appropriately, the side supports 325 will gently contact the hips of the patient on each side therefore aligning the patient over the device such that the patient's anatomy is aligned with the apparatus design which was patterned on the human anatomy.

In one embodiment, ideal patterns include designs that when any given pressure relief chamber is deflated, the pressure relief chambers that remain inflated are still effective in comfortably supporting the weight of the patient such that a low pressure area is created and maintained in the area of the deflated relief chamber region by effectively holding up the patient in the regions where the relief chambers remain inflated. This means that the relief chambers must be neither too large nor too small in any given area or region. In one embodiment, each of the three relief chambers represent around 33% of the total surface area device within a 20×20 square inch area of the sacral region.

With typical support surfaces (e.g., standard hospital bed) a standard mattress or support surface is 36 inches wide. Accordingly, patients using these devices still have ample room between the patient and a side support (or bolster) which allows them to move side to side (laterally). As a result with typical or current support surfaces a patient is not held in a specific location, and thus the typical support surface cannot be anatomy specific.

For a device that is specifically designed to function optimally when located beneath the patient's anatomy in a specific location, then the ability to move around freely over the surface would render that support surface ineffective as the patient and the anatomy specific pattern would not be controlled by the addition of the side bolsters. This differs from other full mattress overlays or mattress support surfaces that are not sized to matched in size to the contact surface of the patient's anatomy but are much larger—i.e. standard bed size of 72 inches×36 inches. Most adult patients (ave 75 kg) unless extremely obese are on average 20 inches wide.

In one embodiment, the pressure relief surface is also contoured to fit the patient's surface topography in the sacral region (i.e., larger in height to the lateral aspects of the relief surface and shorter in height to the center of the pressure relief surface). This contour creates a bowl shape from side to side in the region of the pressure relief surface that compliments the human topography of the sacral region. This is in distinction to the consideration of the internal anatomy, namely blood vessels, muscle and bony anatomy. This internal anatomy is considered in the pattern (not height) of the air cell design which is distinct from considerations of surface topography that dictate the vertical height of the inflated air cells to accommodate variation in the surface contours of the human anatomy. Inflation of the apparatus can result in a bowl shape.

The bowl shape is designed to create an even distribution of pressure when all the air cells of the pressure relief surface are inflated. The result of the bowl shape is to maximally redistribute pressure away from the central area where pressure ulceration is most common—namely at the top of the gluteal fold. The pressure is displaced to a more lateral location towards the hips. The 3-D nature or differences in vertical height throughout the inflated pressure relief surface is not utilized in prior art designs. Further, the diameter or vertical height of the inflated pressure relief chambers that make up the pressure relief surface are specifically designed to be of a suitable height so as not to be so large as to create mal-alignment of the long axis (spine) of the patient but also not of a height that would be to small as to be ineffective as a pressure relief surface. This vertical height is roughly 2-3 inches on average.

Figure 4:
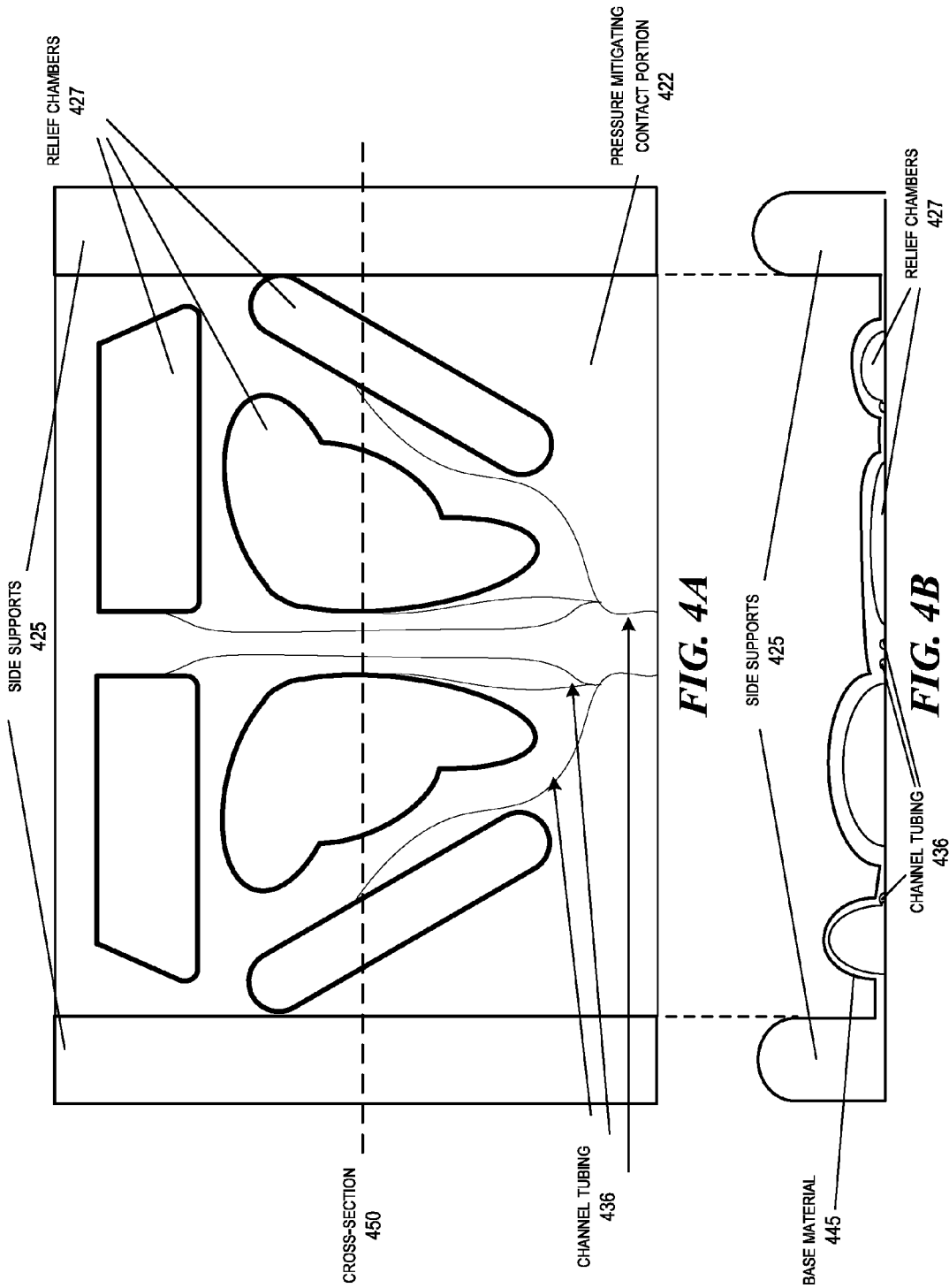
FIG. 4A and FIG. 4B depict top and cross-sectional views, respectively, of an example pressure mitigation support apparatus, according to an embodiment.

FIG. 4A and FIG. 4B depict top and cross-sectional views, respectively, of an example pressure mitigation support apparatus 400, according to an embodiment. The pressure mitigation support apparatus 400 includes side supports 425 and a pressure-mitigating contact portion 422. The pressure-mitigating contact portion 422 includes a plurality of independently pressurized relief chambers 427. The independently pressurized relief chambers 427 are configured in a specific geometric pattern that effectively mitigates contact pressure between a support surface and a specific anatomic region of the patient's body when the specific anatomic region of the patient's body is oriented over an epicenter of the geometric pattern. The pressure mitigation support apparatus 400 may be, for example, the pressure mitigation support apparatus 120 of FIG. 1; although alternative configurations are possible.

As discussed above, the pressure mitigation support apparatus 400 includes channel tubing 436. The channel tubing 436 is separate from the pressure relief surface portion of the device but can be incorporated into the design of the device such that the tubing will follow the seams or channels between the pressure relief surfaces where adjacent independently pressurized relief chambers meet. In one embodiment, the channel(s) are recessed into the seams when the relief chambers 427 are pressurized and/or otherwise inflated. Thus, once the relief chambers 427 are pressurized and/or otherwise inflated, the channel tubing 436 does not make physical contact with the patient. Additionally, the channel tubing 436 does not contribute to the pressure mitigation function of the device or apparatus. That is, the channel tubing 436 serves only to circulate pressure (e.g., air, liquid, etc.) between the seams or recessed channels created by the relief chambers 427.

In one embodiment, the pressure that exits the channels does not originate from the relief chambers of the pressure relief surfaces. For example, the pressure that exits from the multi-channel tubing can originate from its own separate source. The pressure or flow from the pressure channels is controlled by a control system such as, for example, the control system 130 of FIG. 1. The control system can control the pressure (e.g., the air supply) and not by the internal pressure of an air filled bladder that comprises a portion of a pressure relieving surface as is the case when a device is configured as a low air loss surface.

The channel tubing 436 is designed as a passive conduit and not as chamber designed to inflate. The channel tubing 436 may be designed not for low air loss as is the case with previously described low air loss surfaces that leak a low amount of air from the internal reservoir of the inflated support surface but the air channels described here deliver do not leak a high volume of air or gas dedicated only to this purpose and none other. The rate of air flow from the channels is precisely controlled by a flow meter and not dependent on internal pressures created within the device as is the case with the low air low surfaces. The channels may have one or more openings for the release of air. The control of the volume of air delivered and not "lost" from the surface is under strict control for the device as is not the case of low air loss surfaces. (Volume not pressure control) In a low air loss setting, if the openings are blocked by the weight of the patient, the air which is at the set pressure of the pressure relieving air chamber will stop flowing. This is different for the air channels described here where the air is delivered by volume control. If the openings to deliver the air are blocked by the weight of the patient, the pressure of the delivered air will continue to rise until it is greater than the external force blocking the openings of the air channels. This variable pressure is not possible in a low air loss configuration. Volume control delivery in a low air loss setting would also control the pressure within the air chamber of the support surface which is undesirable.

Figure 5:
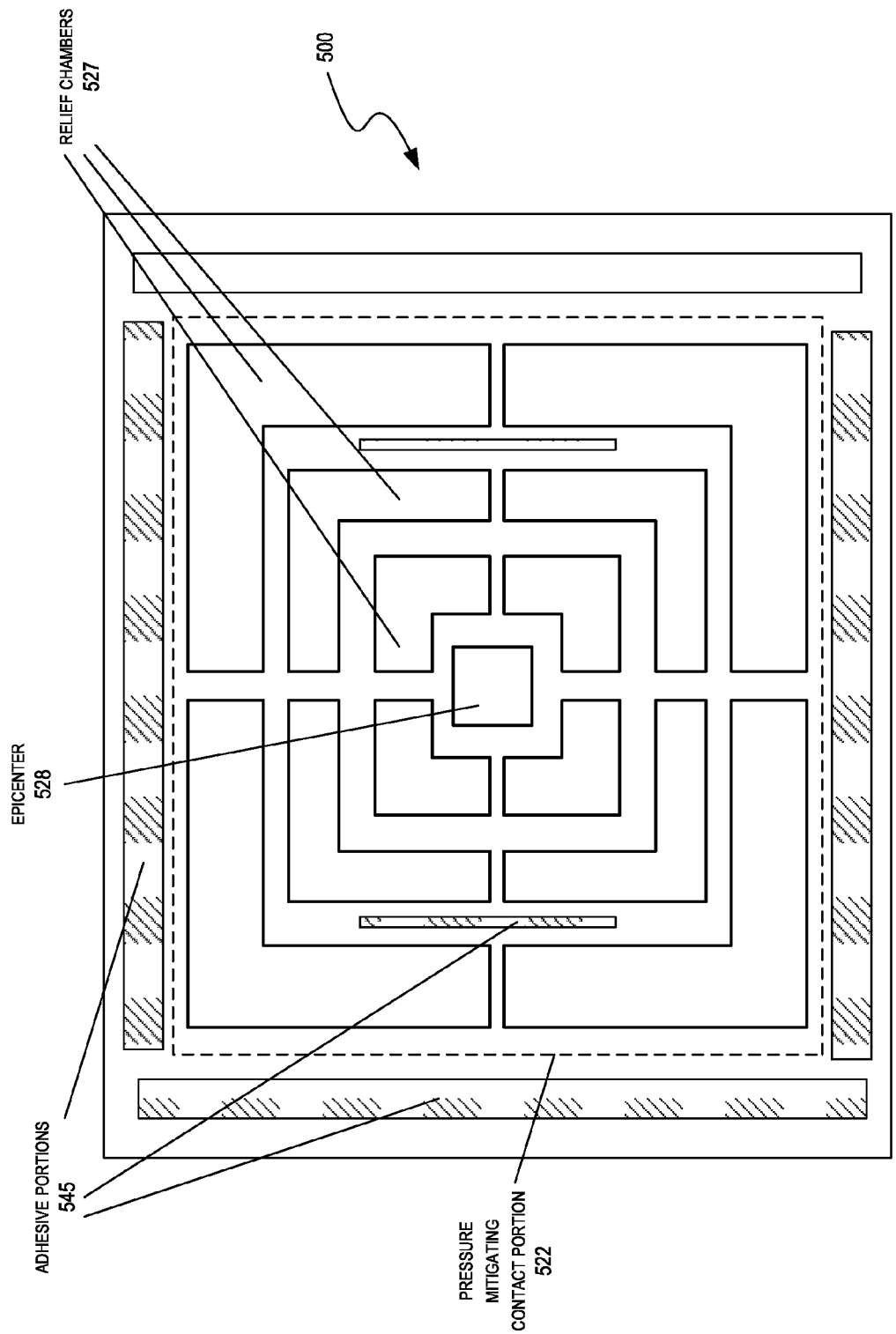
FIG. 5 depicts an example pressure mitigation support apparatus, according to an embodiment.

FIG. 5 depicts an example pressure mitigation support apparatus 500, according to an embodiment. The pressure mitigation support apparatus 500 includes a pressure-mitigating contact portion 222 and one or more adhesive portions 545. The pressure-mitigating contact portion 222 includes a plurality of independently pressurized relief chambers 527. In this example, the independently pressurized relief chambers 527 are configured in a specific geometric "C-shape" pattern that mitigates contact pressure between a support surface and a specific anatomic region of the patient's body when the specific anatomic region of the patient's body is oriented over an epicenter of the geometric pattern. The one or more adhesive portions are interconnected on the mitigation support apparatus 500. The adhesive portion may be configured to actively orient the specific anatomic region of the patient's body over the epicenter 528 of the geometric pattern through one or more biocompatible adhesives. Although the pressure mitigation support apparatus 500 is shown without side supports, it is appreciated that such supports may be included in some embodiments.

In the example, of FIG. 5, the one or more adhesive portions 545 are shown with cross shading. The one or more adhesive portions 545 may be biocompatible adhesive portions that extend along a section of the perimeter of the contact pressure-mitigation support apparatus. Alternatively or additionally, the one or more adhesive portions 545 may extend along at least a section of one or more of the plurality of the independently pressurized relief chambers such as, for example, the "C-shaped" independently pressurized relief chambers.

In one embodiment, the one or more adhesive portions 545 can be adhered directly to the area of concern via a biocompatible adhesive such as, for example, the adhesive material used in common medical band-aids. In this case, the pressure mitigation support apparatus 500 may essentially act as an inflatable band-aid "like" device that could be in the form of the two "C-shapes" around a central area of ulceration or a central area at risk of ulceration.

Figure 6:
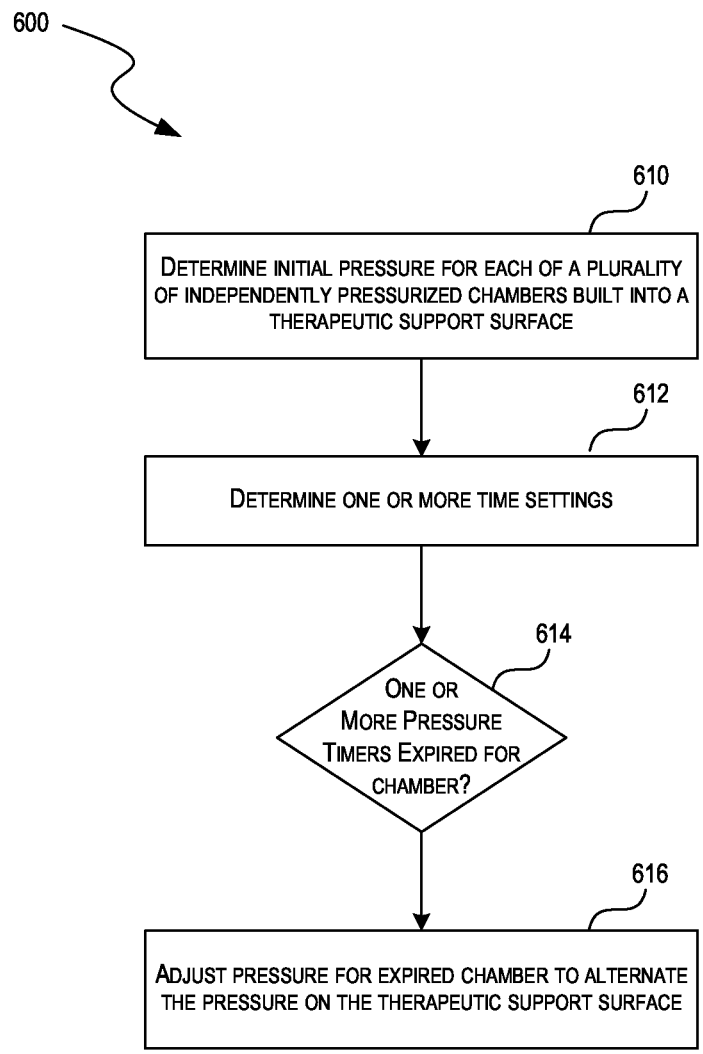
FIG. 6 depicts a flow chart illustrating an example process for coordinated chamber inflation and deflation of a therapeutic surface while the spatial relationship between the patient and the therapeutic surface is controlled by the side-walls of the therapeutic surface.

FIG. 6 depicts a flow chart illustrating an example process 600 for coordinated chamber inflation and deflation of a therapeutic surface to stimulate blood flow and reduce pressure while a spatial relationship between a patient and a therapeutic surface is controlled by side-walls of the therapeutic surface.

As discussed, the inflatable support surface is comprised of the two side walls and a center portion with multiple separate air bladders (or chambers) designed in a specific pattern to best preserve blood flow and reduce pressure when inflated and deflated in a coordinate fashion that is controlled by settings in the air pump control device. Process 600 describes the coordinated chamber inflation and deflation of a therapeutic surface according to one embodiment.

In step 610, an air pump control system such as, for example, air pump control system 130 of FIG. 1 determines an initial pressure for each of a plurality of independently pressurized chambers built into a therapeutic support surface. In step 612, the air pump control system initializes one of more of the settings. The initialization of the setting can include selecting a program and/or one or more pressure timers. The pressure timers can control when and if to change the pressure at an individual chamber. In one embodiment, each chamber has its own timer. However, in other embodiments, some chambers may share timers. Further, any of the chamber timers can be configured to work in concert. In one embodiment, one or more of the initialization settings can be based on the patient (e.g., weight, age, pre-programmed, etc.). In step 614, the air pump control system checks to see if a timer has expired, and if so, in step 616, the air pump control system adjusts the pressure in the associated chamber accordingly.

Figure 7:
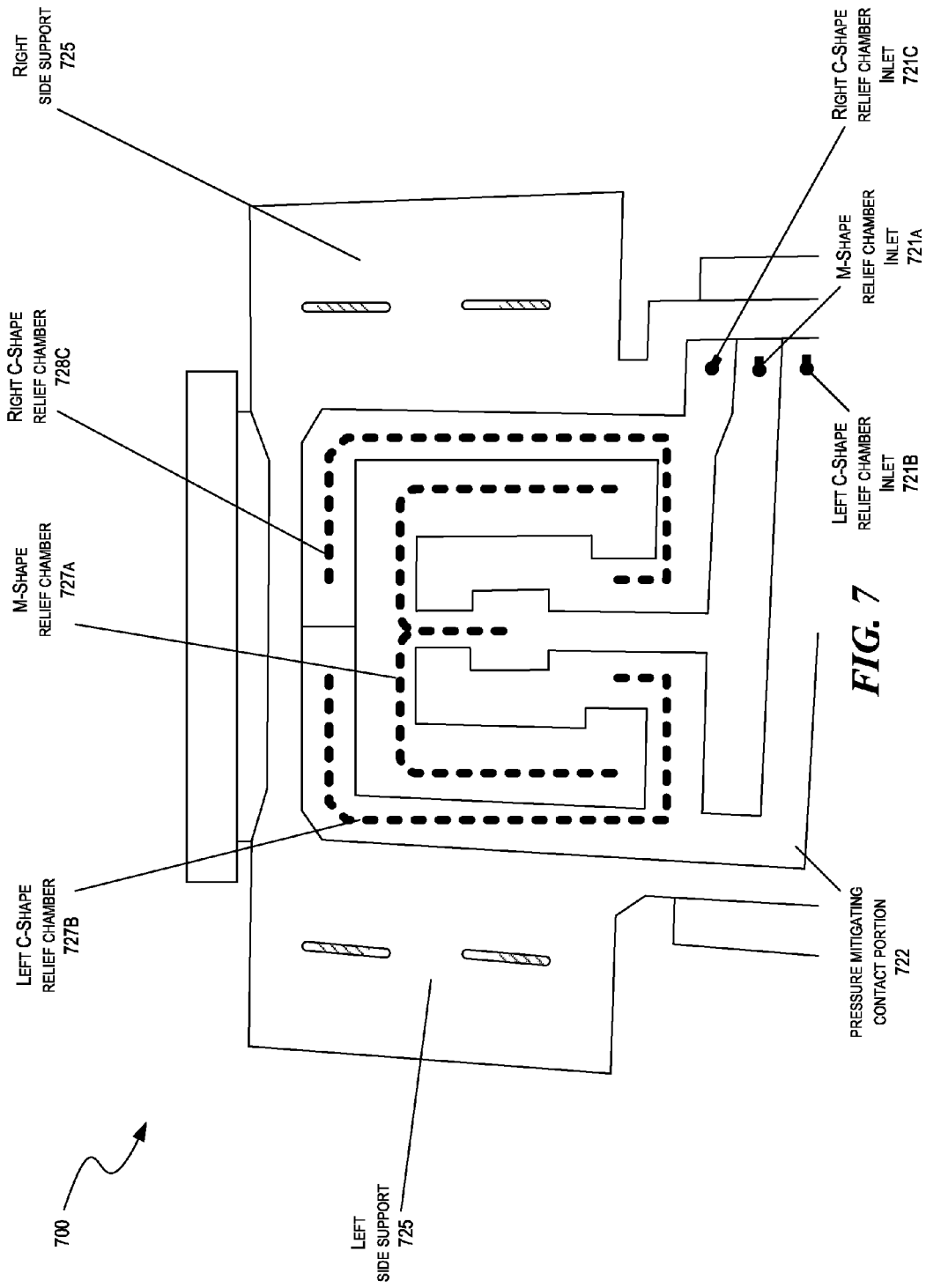
FIG. 7 depicts a schematic diagram illustrating an example pressure mitigation support apparatus, according to an embodiment.

FIG. 7 depicts a schematic diagram illustrating an example pressure mitigation support apparatus 700, according to an embodiment. The pressure mitigation support apparatus 700 includes side supports 725 and a pressure-mitigating contact portion 422. The pressure-mitigating contact portion 722 includes a plurality of independently pressurized relief chambers 727. The pressure mitigation support apparatus 700 may be, for example, the pressure mitigation support apparatus 120 of FIG. 1; although alternative configurations are possible.

In one embodiment, the independently pressurized relief chambers 727 are configured in a specific geometric pattern that effectively mitigates contact pressure between a support surface and a specific anatomic region of the patient's body when the specific anatomic region of the patient's body is oriented over an epicenter of the geometric pattern. For example, in the example of FIG. 7, three independently pressurized relief chambers 727 are shown: M-shaped relief chamber 727a, left c-shaped relief chamber 727b, and right c-shaped relief chamber 728c. These relief chamber receive pressure or air from corresponding inlets 721.

In one embodiment, the geometric pattern includes the first independently pressurized relief chamber 727a which intersects the epicenter of the geographic pattern, and second and third independently pressurized relief chambers, 727b and 727c, respectively, that collectively encompass the first independently pressurized relief chamber. More specifically, in the example of FIG. 7, the first independently pressurized relief chamber 727a generally comprises an M-shape with the epicenter of the geometric pattern residing at the internal angle formed by the intersecting planes of the M-shape, and the second independently pressurized relief chamber 727b generally comprises a C-shape that encompasses a left-most bisection of the first independently pressurized relief chamber, and the third chamber 727c comprises a symmetric mirror image of the second chamber about the bisection of the first chamber.

Figure 8:
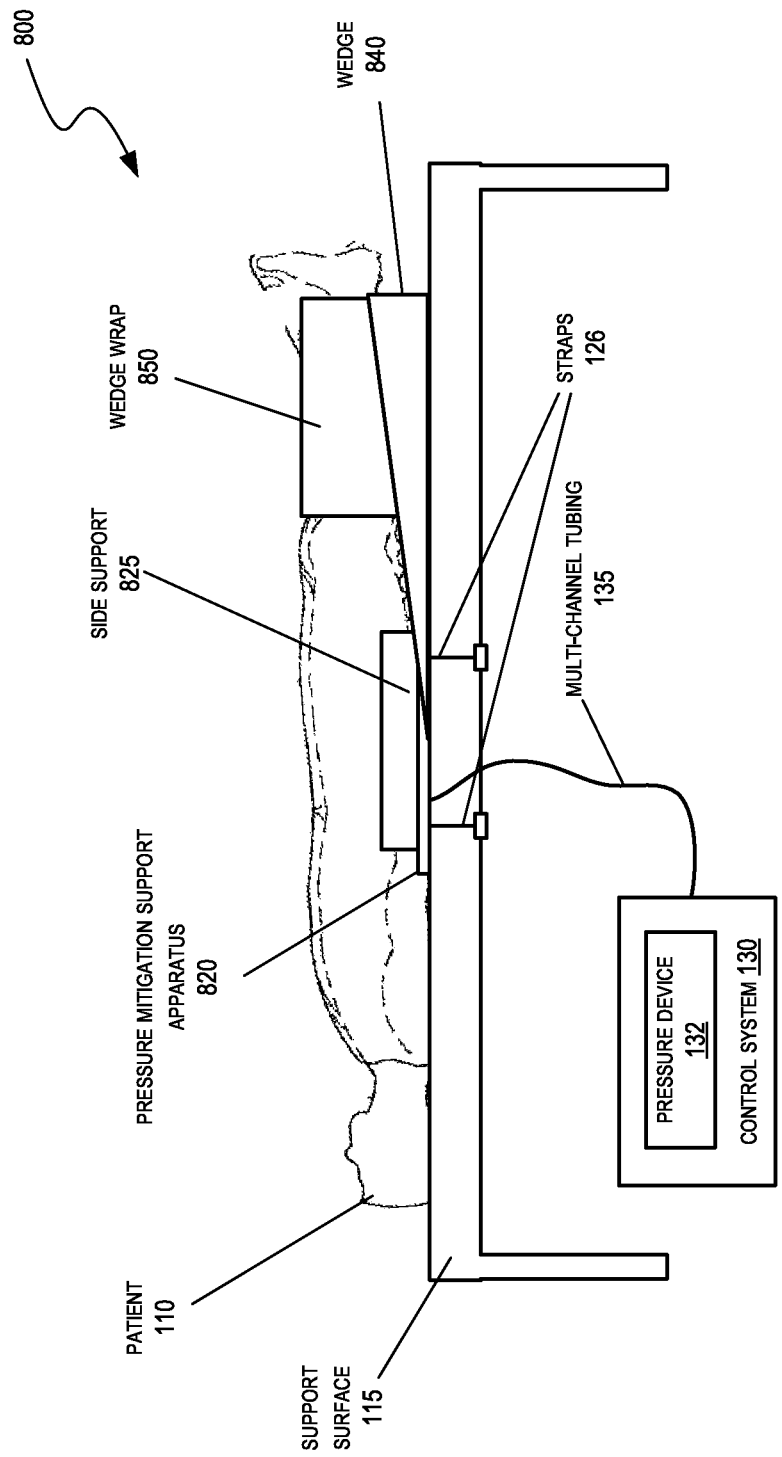
FIG. 8 depicts a side view of an example system for orienting a patient over an anatomy-specific pressure-mitigating contact surface with lower extremity wedge on which the patient rests, according to an embodiment.

FIG. 8 depicts a side view of an example system 800 for orienting a patient over an anatomy-specific pressure-mitigating contact surface with lower extremity wedge on which the patient rests, according to an embodiment. The example of FIG. 8 is similar to the example of FIG. 1, however the pressure mitigation support apparatus 820 includes a lower extremity wedge 840 and an optional wedge wrap 850.

In one embodiment, the lower extremity wedge 840 is an inflatable wedge that is designed to fit (or sit) beneath the lower extremities of the user. The lower extremity wedge 840 can elevate the legs to provide additional benefits to a patient or user. In one embodiment, the lower extremity wedge 840 can be attached to or be part of (integrated into or with) the side supports 825.

In one embodiment, the lower extremity wedge 840 can prevent the migration of the user toward the foot of the bed (lengthwise movement) and/or can act to further maintain the position of the user over the pressure mitigation support (PMS) apparatus 820 in the Y-axis.

As discussed above, in one embodiment, the pressure mitigation support apparatus can comprise an overlay that can be extended behind a patient's lower extremities to include a wedge 840 configured to elevate the legs in order to prevent the user from moving toward the foot of the bed. Accordingly, the wedge 840 aids in the control of the user's location over the pressure mitigation support apparatus. As the side air bolsters (side supports 825) orient the user's location over the pressure mitigation support apparatus so too does the wedge 840 behind the lower extremities by preventing the user from moving toward the foot of the bed when the head of the bed is elevated. In one embodiment, the wedge 840 lifts the lower extremities when in use and protects the user's heals.

In one embodiment, the pressure mitigation support apparatus 820 (or the wedge 840) includes a wedge wrap 850. The wedge wrap 850 can be configured to wrap around the lower extremities to serve both as a deep venous thrombosis prevention device and a pressure ulcer prevention device. Accordingly, in operation, the wedge 840 can lift the lower extremities (e.g., a user's or patient's heels) from the support surface 115 leaving the heels less prone to the formation of pressure ulcers.

In one embodiment, all or part of the wedge 840 can be removably detachable from the pressure relieving portion (i.e., the pressure migration support apparatus 820) or it may be constructed as one unit.

Figure 9:
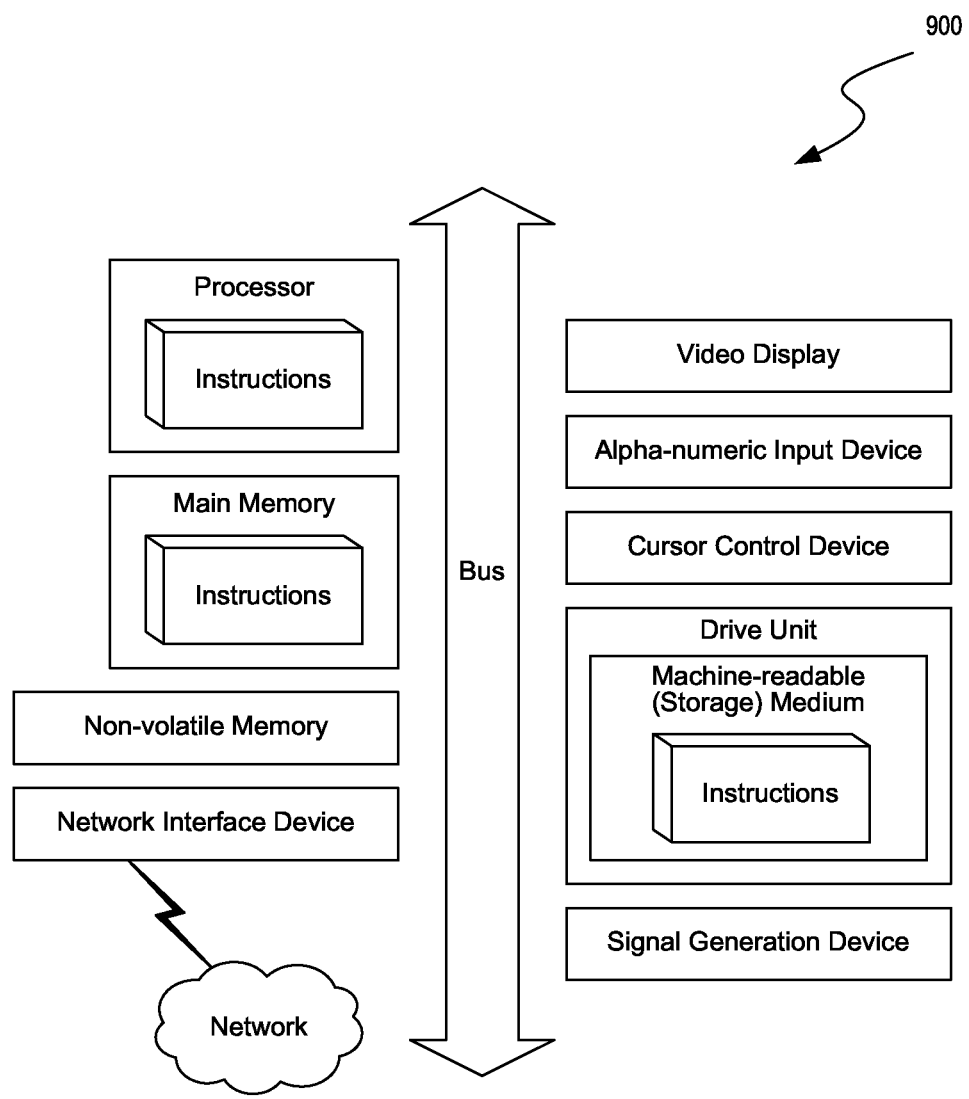
FIG. 9 depicts a diagrammatic representation of a machine in the example form of a computer system within which a set of instructions, for causing the machine to perform any one or more of the methodologies discussed herein, may be executed.

FIG. 9 shows a diagrammatic representation of a machine in the example form of air pump control system 900 within which a set of instructions, for causing the machine to perform any one or more of the methodologies discussed herein, may be executed.

In alternative embodiments, the machine operates as a standalone device or may be connected (e.g., networked) to other machines. In a networked deployment, the machine may operate in the capacity of a server or a client machine in a client-server network environment, or as a peer machine in a peer-to-peer (or distributed) network environment.

The machine may be a server computer, a client computer, a personal computer (PC), a tablet PC, a set-top box (STB), a personal digital assistant (PDA), a cellular telephone, a web appliance, a network router, switch or bridge, or any machine capable of executing a set of instructions (sequential or otherwise) that specify actions to be taken by that machine.

While the machine-readable (storage) medium is shown in an exemplary embodiment to be a single medium, the term "machine-readable (storage) medium" should be taken to include a single medium or multiple media (e.g., a centralized or distributed database, and/or associated caches and servers) that store the one or more sets of instructions. The term "machine-readable medium" or "machine readable storage medium" shall also be taken to include any medium that is capable of storing, encoding or carrying a set of instructions for execution by the machine and that cause the machine to perform any one or more of the methodologies of the present invention.

In general, the routines executed to implement the embodiments of the disclosure, may be implemented as part of an operating system or a specific application, component, program, object, module or sequence of instructions referred to as "computer programs." The computer programs typically comprise one or more instructions set at various times in various memory and storage devices in a computer, and that, when read and executed by one or more processors in a computer, cause the computer to perform operations to execute elements involving the various aspects of the disclosure.

Moreover, while embodiments have been described in the context of fully functioning computers and computer systems, those skilled in the art will appreciate that the various embodiments are capable of being distributed as a program product in a variety of forms, and that the disclosure applies equally regardless of the particular type of machine or computer-readable media used to actually effect the distribution.

Further examples of machine or computer-readable media include but are not limited to recordable type media such as volatile and non-volatile memory devices, floppy and other removable disks, hard disk drives, optical disks (e.g., Compact Disk Read-Only Memory (CD ROMS), Digital Versatile Disks, (DVDs), etc.), among others, and transmission type media such as digital and analog communication links.

Additional Embodiments and Features

Integrated Components

In one embodiment, in addition to the "user orienting" features of the side walls which acts to hold or secure the user over the pressure reduction surface (PRS) such as, for example, the pressure mitigation support apparatus 120 of FIG. 1, in a specific orientation in order to maximize the pressure reduction and redistribution qualities of the surface, the elevated side walls can also act to hold or secure the user over the entirety of the air cells of the PRS such that no portion of the air cells of the PRS is uncovered. In other words, no portion of the air cells extend beyond the downward force of the user. If the air cells are allowed to extend beyond the downward force, and therefore not be completely covered by the user, then the air within the air cells could preferentially fill the portion of the air cell which remained uncovered by the user causing a "ballooning effect" of the uncovered portion of the air cell at the portion not covered by the user.

In one embodiment, the PRS is designed to fit to the size of the user (or fitted). The ballooning of the uncovered portion of the air cells can defeat the lifting effect produced by the air cells that occurs when the air cell is covered in its entirety by the user. Thus, as a result of the ballooning, increased air pressure within the air cells can be required to create the desired lifting of the user. Accordingly, in some instances, the lowest possible internal air pressure that could be used to lift the user may not be effective in this regard and additional, higher internal pressures could be necessary to perform the lifting. The increased pressures that would defeat the pressure reducing aim of the device. The side walls act to keep the user on top of the PRS as well as orient the user over that surface. If the side wall did not exist to frame the PRS, then the user would be free to move off the PRS allowing ballooning of the air cells on the opposite side and in addition the anatomy of the user's sacral region would not be in correct alignment with the geometry of the PRS. The side walls therefore function in this dual capacity.

In one embodiment, the inflatable portion of the device can have a specific orientation on top of the mattress or chair upon which it rests such that there is a side specific to the user contact and a side that is specific to the contact of the surface upon which it rests. In this example, the upward facing side of the PRS has a covering which is breathable and suited for direct skin contact while the down side of the PRS that is in contact with the mattress or chair is covered with a less non porous material which has a reduced coefficient of friction that is less suitable for direct skin contact. The result of this construction can act to protect the user from the negative effects of shear strain on the skin as the device will preferentially slide over the underlying surface as the user stays in position with respect to the device. This construction can also act to prevent the user from moving from the proper orientation over the PRS of the inflatable portion of the device.

In one embodiment, the maximum pressure reduction and redistribution by the PRS is achieved when the user is oriented in a specific location over the pattern of the PRS. The side walls can control the users location over the surface in the x axis while the bed, when in a V-position with the legs elevated and the head elevated, acts to center the user over the PRS in the y axis.

In one embodiment, the apparatus consists consisting of an inflatable portion (pressure relieving surface), connector tubing and a computer controlled air pump can be incorporated into a support surface such as a mattress. In one embodiment, the additional components can be incorporated or integrated into support surface (e.g., reside within or under the support surface). Alternatively, the additional components can be attached to the outer surface of the support surface or mattress such the components become an integral part of the support surface without being inside the support surface. For example, the component can be attached to or attachable to the bed frame which supports the support surface or mattress. Alternatively or additionally, some or all of the components can also rest passively on the support surface without being physically attached to the support surface.

In one embodiment, the addition of the device (or apparatus) to the support surface enhances the functional pressure relief characteristics of the support surface to which it is added or attached or inserted into.

In one embodiment, the combination of the device and a support surface will not affect the ability of the device to perform its intended function as a pressure relief surface that is designed to orient the users anatomy with respect to the pattern of the pressure relief surface of the device through the use of elevated side walls intended to hold the users location in a specific manner. The location specific relationship will enhance the pressure relief capabilities of the device.

Computer-Controlled Pump

In one embodiment, a computer controlled pump that controls the inflatable portion of the device can be programmed with the specific weight of the user so as to deliver the correct user-specific pressures required for optimal pressure relief and redistribution for that particular user. The pump can continuously adjust the air pressures within the inflatable portion of the device so as to achieve predetermined preset internal air pressures within the air cells in order to achieve the optimal interface pressures between the user and the pressure relief surface of the device. This process is accomplished by continuously adding or removing air from the air cells to adjust to the varying load placed on the pressure relief surface by the user.

In one embodiment, the position of the user (e.g., supine, 30 degrees, 90 degrees) is entered into the pump along with the weight of the user so as to calculate the ideal internal air pressures of the air cell of the pressure relief surface to produce the ideal pressure relief characteristic for the device. That is the information is provided to a pump control device which generates a program that indicates appropriate pressures for each of the air cells over time. The pump control device then continuously controls the pump to provide the continuously changing pressures that are indicated by the program.

In one embodiment, the specific nature (e.g., of the stretcher pad—less than 3 inches, standard hospital mattress—non powered more than 3 inches, alternating pressure air mattress, etc.) of the support surface on which the inflatable overlay rests is entered into the computer controlled air pump in order to calculate the ideal internal pressure for the air cell of the pressure relief surface in order to produce the most effective pressure relief and redistribution.

In one embodiment, the pre-determined pressure time cycle programmed into the pump is used to coordinate the inflation and deflation of each air cell with respect to each other air cell of the inflatable portion of the device so as to produce an effective pressure relief and redistribution surface. The exact internal air pressures for a specific user can be calculated based the weight of that specific user, the surface the overlay is resting on, and the position of the bed (e.g., 0 degree, 30 degree, 90 degree) on which the overlay rests or is incorporated into. There is an algorithm programmed into the pump which calculates the exact pressures used for each user based on these variable that are entered for each user.

In one embodiment, the pump can acquire the programmable data regarding utilization, and this data can be sent via direct download or wirelessly to the computer controlled pump from a central database.

In one embodiment, the pump can utilize a silent valve system so as not to disturb the user.

In one embodiment, the air circulation portion of the inflatable overlay is comprised of a perforated sheet that covers the pressure relief surface and is supplied by a separate low pressure high flow pump to produce air circulating between the surface of the overlay and the user at the interface of the two. In this example, the chamber supplied with high flow low pressure air has no pressure relief capabilities and does not represent low air loss from the pressure relief air cells that are responsible for support of the weight of the user as in a low air loss configuration where the air in circulation between the user and the support surface is leaked directly from the pressure relieving air cells of the support surface.

In one embodiment, there is a pop off valve in the inflated side wall air cell which contains in a specific location the user over the pressure relief surface of the overlay such that if there is excess pressure placed on the side air wall the internal air is vented from the side air wall so as to prevent a blow out of the side air cell.

In one embodiment, the device can be used solely for the purpose of comfort of the user. For example, the device can be used during travel to prevent soreness and/or fatigue associated with long trips such as on airplane or bus or car.

In one embodiment, the pump and/or controller can be powered by ac or dc current.

In one embodiment, the device system with one or more of the pump, tubing, and inflatable portion (as described in the original non provisional) can be powered by one or more batteries.

In one embodiment, the device can be attached to any support surface, i.e., a chair or a bed. Alternatively or additionally, the device can be incorporated into any support surface, i.e., a bed or a chair. Alternatively or additionally, or the device can placed on top of any support surface i.e., a bed or a chair.

In one embodiment, the side walls act to hold the user over the PRS such that the entire surface area of the air cells that comprise the PRS is covered by the downward force of the user in order to prevent the ballooning of the air cells in areas not covered by the user by leaving no portion of the air cells uncovered at any location in order to increase the ability to reduce and redistribute interface pressure at the lowest internal air cell pressures possible.

In one embodiment, the side of the inflatable portion of the device that is in contact with the user's skin is breathable and the portion that is in contact with the surface upon which it rests is non-porous and has a low coefficient of friction so as to reduce the shear at the interface between the user and the device while this enables the user to remain in the proper orientation over the PRS of the device.

In one embodiment, a contact pressure mitigation support apparatus includes a pressure-mitigating contact portion and a plurality of elevated side support portions. The pressure-mitigating contact portion is interconnected on a base material and includes a plurality of independently pressurized chambers configured in a specific geometric pattern that is designed to mitigate contact pressure between a support surface (e.g., bed or chair) and a specific anatomic region of a patient's body when the specific anatomic region of the patient's body is oriented over an epicenter of the geometric pattern. The plurality of elevated side support portions is also interconnected on the base material and configured to actively orient the specific anatomic region of the patient's body over the epicenter of the geometric pattern.

In an embodiment, the contact pressure between the support surface and the specific anatomic region of the patient's body is mitigated by alternating the pressure in one or more of the plurality of independently pressurized relief chambers.

In an embodiment, the elevated side support portions are configured to actively orient the specific anatomic region of the patient's body over the epicenter of the geometric pattern when pressurized.

In an embodiment, the contact pressure mitigation support apparatus further includes one or more straps interconnected on the base material, wherein the one or more straps are configured to secure the pressure mitigation support apparatus to the support surface.

In an embodiment, the contact pressure mitigation support apparatus further includes a position sensor interconnected on the base material. The position sensor is configured to confirm that the specific anatomic region of the patient's body is oriented over the epicenter of the geometric pattern.

In an embodiment, the contact pressure mitigation support apparatus further includes a radio frequency (RF) transceiver interconnected on the base material and configured to wirelessly transmit the confirmation that the specific anatomic region of the patient's body is over the epicenter of the geometric pattern and/or receive instructions for individual chamber pressurization, etc.

In an embodiment, the pressure-mitigating contact portion is contoured to fit the patient's surface topography in the sacral region.

In an embodiment, to fit the patient's surface topography, the plurality of independently pressurized relief chambers are shorter in height in the center of the pressure-mitigating contact portion and taller in height on the edges of the pressure-mitigating contact portion.

In an embodiment, a surface area of the pressure-mitigating contact portion is designed to match the size of contact with the specific anatomic region of the patient's body.

In an embodiment, a surface area of the pressure-mitigating contact portion is designed to be less than the size of contact with the specific anatomic region of the patient's body.

In an embodiment, the length and the width of the pressure-mitigating contact portion are between fifteen and thirty inches.

In an embodiment, the plurality of elevated side support portions are elevated two or more inches in vertical height above the average surface height of the pressure-mitigating contact portion.

In an embodiment, the plurality of elevated side support portions are elevated in vertical height above the average surface height of the pressure-mitigating contact portion so as to create a barrier to lateral movement.

In an embodiment, the side support portions comprise independently pressurized chambers.

In an embodiment, the side support portions include a recess to support the patient's elbow.

In an embodiment, the independently pressurized relief chambers are configured to be independently pressurized with a gas.

In an embodiment, the independently pressurized chambers are configured to be independently pressurized with a liquid.

In an embodiment, the support surface comprises a mattress.

In an embodiment, the specific anatomic region of the patient's body comprises the sacral region.

In an embodiment, to actively orient the specific anatomic region of the patient's body over the epicenter of the geometric pattern, the plurality of side support portions are configured to confine lateral movement of the patient.

In an embodiment, to actively orient the specific anatomic region of the patient's body over the epicenter of the geometric pattern, the epicenter of the geometric pattern is overlaid on a V-shape in the support surface such that the epicenter of the apparatus resides over the low point of the support surface that is conformed into the V-shape upon which the apparatus rests.

In an embodiment, the anatomic region of the patient's body is segmented into various sub-regions and the geometric pattern is configured such that each of the independently pressurized chambers correspond to one of the various sub-regions.

In an embodiment, the independently pressurized chambers fit to the corresponding sub-region.

In an embodiment, the geometric pattern is symmetric and non-repeating in nature.

In an embodiment, the contact pressure mitigation support apparatus includes one or more channel tubes interconnected on the base material, the channel tubes configured to deliver pressure to the independently pressurized relief chambers.

In an embodiment, the contact pressure mitigation support apparatus includes one or more channel tubes interconnected on the base material, the channel tubes can be configured to deliver a gas (i.e., air or oxygen.) from one or more openings in the channel tubes. In this case, the channel tubes are not part of the pressure relieving surface (i.e., low air loss surface) and the gas delivered from the channel tubes is from a source independent from the pressure controlled supply of gas to the pressurized relief surfaces. That is, the gas delivered by the channel tubes is high volume and under volume control regulation.

In an embodiment, the one or more channel tubes follow seams between the independently pressurized relief chambers.

In an embodiment, the seams are recessed between the independently pressurized relief chambers when one or more of the independently pressurized relief chambers is pressurized.

In one embodiment, a partial body alternating contact pressure mattress overlay device is disclosed. The partial body alternating contact pressure mattress overlay device includes a plurality of independently pressurized chambers, a plurality of elevated side supports, and one or more straps. The plurality of independently pressurized chambers are configured in a geometric pattern that mitigates contact pressure between a support surface and a specific anatomic region of a patient's body when the specific anatomic region is oriented over an epicenter of the geometric pattern. The plurality of elevated side support portions are configured to actively orient the specific anatomic region over the epicenter of the geometric pattern. The one or more straps are configured to secure the pressure mitigation support device to the support surface.

In an embodiment, the partial body alternating contact pressure mattress overlay device further includes a radio frequency identification (RFID) detector configured to configured to detect whether the specific anatomic region of the patient's body is over the epicenter of the geometric pattern.

In an embodiment, the partial body alternating contact pressure mattress overlay device further includes one or more pressure sensors configured to detect the real-time pressure of each of the independently pressurized chambers.

In one embodiment, an alternating contact pressure mattress includes a mattress, a pressure-mitigating contact portion and a plurality of elevated side support portions. The pressure-mitigating contact portion includes a plurality of independently pressurized relief chambers interconnected on the mattress, wherein the independently pressurized relief chambers are configured in a geometric pattern that mitigates contact pressure between a support surface and a specific anatomic region of a patient's body when the specific anatomic region of the patient's body is oriented over an epicenter of the geometric pattern. The plurality of elevated side support portions are interconnected on the mattress and configured to actively orient the specific anatomic region of the patient's body over the epicenter of the geometric pattern.

In one embodiment, a contact pressure mitigation system is disclosed. The contact pressure mitigation system includes a pressure-mitigating support apparatus and a controller. The pressure-mitigating support apparatus includes a base material, a pressure-mitigating contact portion including a plurality of independently pressurized relief chambers interconnected on the base material, wherein the independently pressurized relief chambers are configured in a geometric pattern that mitigates contact pressure between a support surface and a specific anatomic region of a patient's body when the specific anatomic region of the patient's body is oriented over an epicenter of the geometric pattern, and a plurality of elevated side support portions interconnected on the base material, wherein the elevated side support portions are configured to actively orient the specific anatomic region of the patient's body over the epicenter of the geometric pattern. The controller is configured to regulate the pressure of each of the independently pressurized relief chambers.

In one embodiment, a contact pressure-mitigation support apparatus includes a base material, a pressure-mitigating contact portion, and a biocompatible adhesive portion. The pressure-mitigating contact portion can include a plurality of independently pressurized relief chambers interconnected on the base material. The independently pressurized relief chambers can be configured in a geometric pattern that mitigates contact pressure between a support surface and a specific anatomic region of a patient's body when pressure in the independently pressurized relief chambers is alternated and the specific anatomic region of the patient's body is oriented over an epicenter of the geometric pattern. The biocompatible adhesive portion interconnected on the base material is configured to actively orient the specific anatomic region of the patient's body over the epicenter of the geometric pattern.

In an embodiment, the biocompatible adhesive portion extends along at least a section of the perimeter of the contact pressure-mitigation support apparatus. The adhesive may be in direct contact with the skin of the user.

In an embodiment, the biocompatible adhesive portion extends along at least a section of one or more of the plurality of the independently pressurized relief chambers.

CONCLUSION

Unless the context clearly requires otherwise, throughout the description and the claims, the words "comprise," "comprising," and the like are to be construed in an inclusive sense, as opposed to an exclusive or exhaustive sense; that is to say, in the sense of "including, but not limited to." As used herein, the terms "connected," "coupled," or any variant thereof, means any connection or coupling, either direct or indirect, between two or more elements; the coupling of connection between the elements can be physical, logical or a combination thereof. Additionally, the words "herein," "above," "below" and words of similar import, when used in this application, shall refer to this application as a whole and not to any particular portions of this application. Where the context permits, words in the above Detailed Description using the singular or plural number may also include the plural or singular number respectively. The word "or," in reference to a list of two or more items, covers all of the following interpretations of the word: any of the items in the list, all of the items in the list, and any combination of the items in the list.

The above-detailed description of embodiments of the disclosure is not intended to be exhaustive or to limit the teachings to the precise form disclosed above. While specific embodiments of, and examples for, the disclosure are described above for illustrative purposes, various equivalent modifications are possible within the scope of the disclosure, as those skilled in the relevant art will recognize. For example, while processes or blocks are presented in a given order, alternative embodiments may perform routines having steps, or employ systems having blocks, in a different order, and some processes or blocks may be deleted, moved, added, subdivided, combined and/or modified to provide alternative or subcombinations. Each of these processes or blocks may be implemented in a variety of different ways. Also, while processes or blocks are at times shown as being performed in series, these processes or blocks may instead be performed in parallel, or may be performed at different times. Further, any specific numbers noted herein are only examples; alternative implementations may employ differing values or ranges.

The teachings of the disclosure provided herein can be applied to other systems, not necessarily the system described above. The elements and acts of the various embodiments described above can be combined to provide further embodiments.

What is claimed is:

1. A contact pressure-mitigation support apparatus comprising:
    a base material;
    a pressure-mitigating contact portion including a plurality of independently pressurized relief chambers interconnected on the base material, wherein the independently pressurized relief chambers are configured in a geometric pattern that mitigates contact pressure between a support surface and a specific anatomic region of a user's body when pressure in the independently pressurized relief chambers is alternated and the specific anatomic region of the user's body is oriented over an epicenter of the geometric pattern;
    a plurality of elevated side support portions interconnected on the base material and configured to actively orient the specific anatomic region of the user's body laterally over the epicenter of the geometric pattern; and
    a wedge portion interconnected on the base material and configured to actively orient the specific anatomic region of the user's body lengthwise over the epicenter of the geometric pattern.

2. The contact pressure mitigation support apparatus of claim 1, wherein the wedge portion is configured to separate at least a portion of the user's lower extremities from the support surface.

3. The contact pressure mitigation support apparatus of claim 2, wherein the at least a portion of the user's lower extremities include the user's heels.

4. The contact pressure mitigation support apparatus of claim 3, wherein the pressure-mitigating contact portion of the contact pressure-mitigation support apparatus is fitted to the user's body such that, when in use, the pressure-mitigating contact portion does not extend lengthwise beyond the user's body.

5. The contact pressure mitigation support apparatus of claim 1, wherein the wedge portion further comprises a plurality of independently pressurized relief chambers interconnected on the wedge portion and configured in a second geometric pattern that mitigates contact pressure between the support surface and the user's lower extremities when pressure in the independently pressurized relief chambers interconnected on the wedge portion is alternated.

6. The contact pressure mitigation support apparatus of claim 1, further comprising:
    a wedge wrap portion interconnected on the base material and configured to wrap around the user's lower extremities to serve as a deep venous thrombosis prevention device.

7. The contact pressure mitigation support apparatus of claim 1, further comprising:
    a wedge wrap portion interconnected on the wedge portion and configured to wrap around the user's lower extremities to serve as a deep venous thrombosis prevention device.

8. The contact pressure mitigation support apparatus of claim 1, wherein the pressure-mitigating contact portion of the contact pressure-mitigation support apparatus is fitted to the user's body such that, when in use, the pressure-mitigating contact portion is completely covered by the user.

9. The contact pressure mitigation support apparatus of claim 1, wherein the pressure-mitigating contact portion of the contact pressure-mitigation support apparatus is fitted to the user's body such that, when in use, the pressure-mitigating contact portion does not extend laterally beyond the user's body.

10. The contact pressure mitigation support apparatus of claim 1, wherein the wedge portion interconnected on the base material is configurably detachable from the base material.

11. The contact pressure mitigation support apparatus of claim 1, wherein the contact pressure mitigation support apparatus comprises an overlay.

12. The contact pressure mitigation support apparatus of claim 1, wherein the geometric pattern includes a first independently pressurized relief chamber that intersects the epicenter of the geographic pattern, and second and third independently pressurized relief chambers that collectively encompass the first independently pressurized relief chamber.

13. The contact pressure mitigation support apparatus of claim 1, wherein the pressure-mitigating contact portion of the contact pressure-mitigation support apparatus is fitted to the user's body such that when pressure in the independently pressurized relief chambers is alternated and the specific anatomic region of the user's body is oriented over the epicenter of the geometric pattern, the pressure-mitigating contact portion does not extend laterally or lengthwise beyond the user's body.

14. The contact pressure-mitigation support apparatus of claim 1, wherein the base material further comprises a first side having a first material disposed thereon and a second side having a second material disposed therein, and wherein the first material is configured for direct contact with the user's body and the second material is configured for direct contact with the support surface.

15. The contact pressure-mitigation support apparatus of claim 14, wherein the first material has a coefficient of friction that is greater than the coefficient of friction of the second material.

16. The contact pressure-mitigation support apparatus of claim 14, wherein the first material is breathable.

17. The contact pressure-mitigation support apparatus of claim 14, wherein the first material is more porous than the second material.

18. The contact pressure mitigation support apparatus of claim 1, wherein the contact pressure between the support surface and the specific anatomic region of the patient's body is mitigated by alternating the pressure in one or more of the plurality of independently pressurized relief chambers.

19. The contact pressure mitigation support apparatus of claim 1, wherein the elevated side support portions are configured to actively orient the specific anatomic region of the patient's body over the epicenter of the geometric pattern when pressurized.

20. A contact pressure-mitigating support surface comprising:
a support apparatus;
a pressure-mitigating contact portion including a plurality of independently pressurized relief chambers incorporated in the support apparatus and configured in a geometric pattern that mitigates contact pressure between the support apparatus and a specific anatomic region of a user's body when the specific anatomic region of the user's body is oriented over an epicenter of the geometric pattern;
a plurality of elevated side support portions incorporated in the support apparatus and configured to actively orient the specific anatomic region of the user's body over the epicenter of the geometric pattern; and
a wedge portion incorporated in the support apparatus and configured to actively orient the specific anatomic region of the user's body lengthwise over the epicenter of the geometric pattern.

21. The contact pressure mitigation support surface of claim 20, wherein the wedge portion is configured to isolate at least a portion of the user's lower extremities from the support surface.

22. The contact pressure mitigation support surface of claim 20, further comprising:
a plurality of independently pressurized relief chambers interconnected on the wedge portion and configured in a second geometric pattern that mitigates contact pressure between the support surface and the user's lower extremities when pressure in the independently pressurized relief chambers interconnected on the wedge portion is alternated.

23. The contact pressure mitigation support surface of claim 20, further comprising:
a wedge wrap portion incorporated in the support apparatus and configured to wrap around the user's lower extremities to serve as a deep venous thrombosis prevention device.

24. The contact pressure mitigation support surface of claim 20, further comprising:
one or more channel tubes incorporated in the support apparatus and configured to deliver pressure to the independently pressurized relief chambers;
a pump incorporated in the support apparatus and configured to pressurize each of the independently pressurized relief chambers;
a controller incorporated in the support apparatus and configured to regulate the pump.

25. The contact pressure mitigation support surface of claim 20, wherein the controller is further configured to regulate the pump to control each of the independently pressurized relief chambers based on a specific weight of the user, and wherein the specific weight of the user is programmable by an operator or the user via an interface on the controller.

26. A contact pressure-mitigating system comprising:
a contact pressure-mitigation support apparatus including a base material, a pressure-mitigating contact portion including a plurality of independently pressurized relief chambers interconnected on the base material, wherein the independently pressurized relief chambers are configured in a geometric pattern that mitigates contact pressure between a support surface and a specific anatomic region of a user's body when pressure in the independently pressurized relief chambers is alternated and the specific anatomic region of the user's body is oriented over an epicenter of the geometric pattern, a plurality of elevated side support portions interconnected on the base material and configured to actively orient the specific anatomic region of the user's body laterally over the epicenter of the geometric pattern, and a wedge portion interconnected on the base material and configured to actively orient the specific anatomic region of the user's body lengthwise over the epicenter of the geometric pattern;

a pump configured to pressurize each of the independently pressurized relief chambers; and a controller configured to regulate pressure provided by the pump.

27. The contact pressure mitigation system of claim 26, wherein the wedge portion is configured to separate at least a portion of the user's lower extremities from the support surface, and wherein the wedge portion further comprises a plurality of independently pressurized relief chambers interconnected on the wedge portion and configured in a second geometric pattern that mitigates contact pressure between the support surface and the user's lower extremities when pressure in the independently pressurized relief chambers interconnected on the wedge portion is alternated.

28. The contact pressure mitigation system of claim 26, the contact pressure-mitigation support apparatus further comprising:
  a wedge wrap portion interconnected on the base material and configured to wrap around the user's lower extremities to serve as a deep venous thrombosis prevention device.

29. The contact pressure mitigation system of claim 26, the contact pressure-mitigation support apparatus further comprising:
  a power source configured to provide power to one or more of the pump and the controller,
  wherein the power source provides alternative current or direct current to the pump and the controller.

30. A partial body alternating contact pressure overlay device comprising:
  a base material;
  a pressure-mitigating contact portion including a plurality of independently pressurized relief chambers interconnected on the base material, wherein the independently pressurized relief chambers are configured in a geometric pattern that mitigates contact pressure between a support surface and a specific anatomic region of a user's body when pressure in the independently pressurized relief chambers is alternated and the specific anatomic region of the user's body is oriented over an epicenter of the geometric pattern;
  a plurality of elevated side support portions interconnected on the base material and configured to actively orient the specific anatomic region of the user's body laterally over the epicenter of the geometric pattern;
  a wedge portion interconnected on the base material and configured to actively orient the specific anatomic region of the user's body lengthwise over the epicenter of the geometric pattern,
    wherein the geometric pattern includes a first independently pressurized relief chamber that intersects the epicenter of the geographic pattern, and second and third independently pressurized relief chambers that collectively encompass the first independently pressurized relief chamber; and
  a wedge wrap portion interconnected on the base material and configured to wrap around the user's lower extremities to serve as a deep venous thrombosis prevention device.

\* \* \* \* \*